Figure 3:
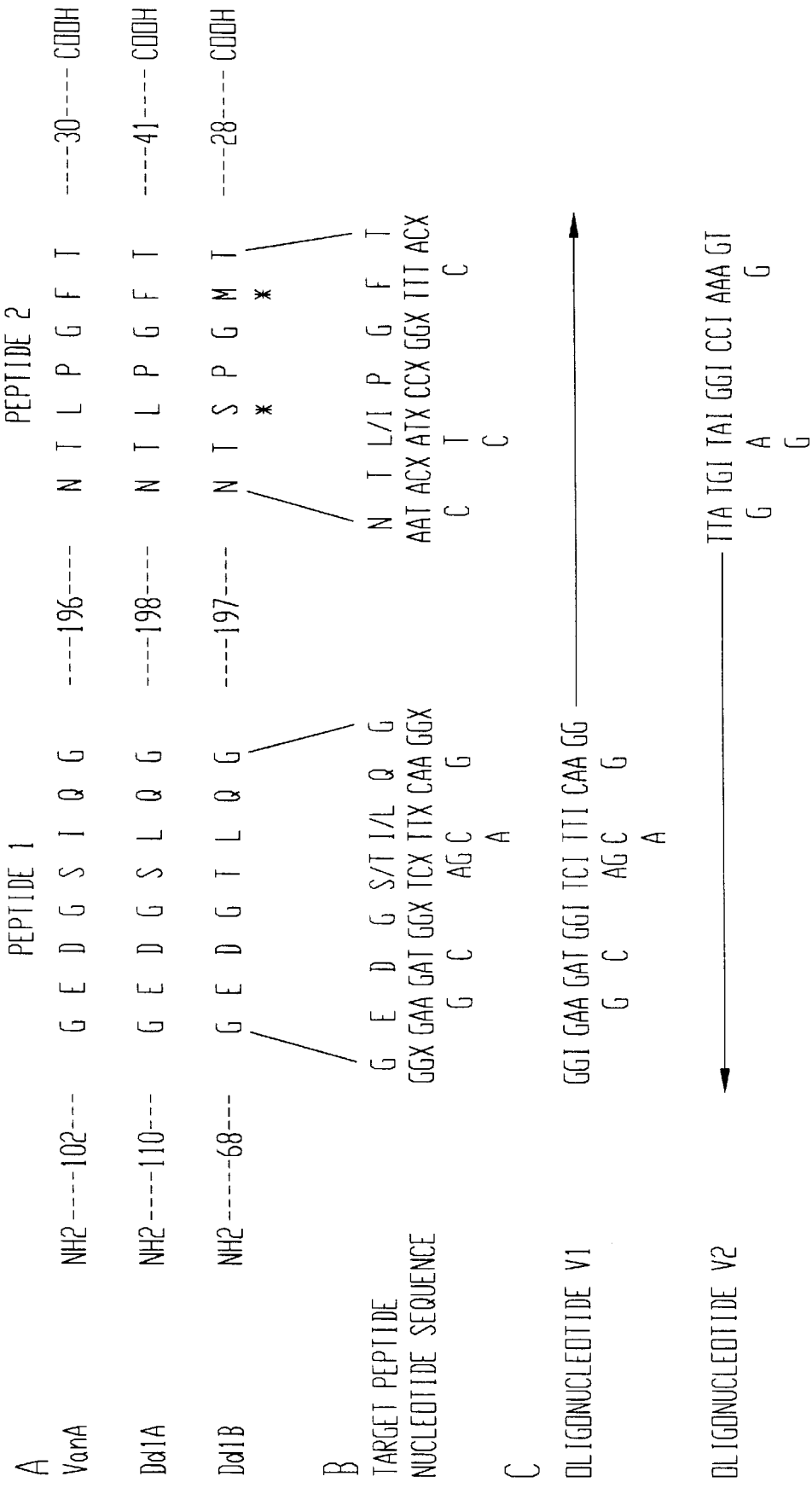

United States Patent [19]
Arthur et al.

[11] Patent Number: 6,087,106
[45] Date of Patent: Jul. 11, 2000

[54] NUCLEIC ACIDS CONFERRING AND INDUCIBLE RESISTANCE TO GLYCOPEPTIDES PARTICULARLY IN GRAM-POSITIVE BACTERIA

[75] Inventors: Michel Arthur, Paris; Sylvie Dutka-Malen, Fresnes; Stefan Evers; Patrice Courvalin, both of Paris, all of France

[73] Assignee: Institut Pasteur, Paris Cedex, France

[21] Appl. No.: 09/064,033

[22] Filed: Apr. 22, 1998

Related U.S. Application Data

[63] Continuation of application No. 08/454,196, filed as application No. PCT/FR93/01264, Dec. 17, 1993, Pat. No. 5,770,361.

[30] Foreign Application Priority Data

Dec. 18, 1992 [FR] France ................................. 92-15671
Jul. 7, 1993 [FR] France ................................. 93-08356

[51] Int. Cl.[7] .............................. C12Q 1/68; C07H 21/02; C07H 21/04
[52] U.S. Cl. .............................. 435/6; 536/22.1; 536/23.1
[58] Field of Search .................................... 536/22.1, 23.1

[56] References Cited

PUBLICATIONS

FESM Microbiol.Letters. vol. 70, pp. 101–106 Al–Obeid et al, 1990.

*Primary Examiner*—Eggerton A. Campbell
*Attorney, Agent, or Firm*—Oblon, Spivak, McClelland, Maier & Neustadt, P.C.

[57] ABSTRACT

The invention relates to a protein VanB involved, in Gram-positive bacteria, in resistance to glycopeptides, particularly to vancomycine, said resistance being of the type inducible by the vancomycine and non-inducible by teicoplanine. The invention also relates to the utilisation of fragments of nucleotides of the gene van B for the detection of resistances to glycopeptides.

24 Claims, 7 Drawing Sheets

```
                                                                      RBS
GAGCGTGTGCTGCGAGATACCACAGAAAACAATCAGAATTGTCTTAACTTTGAAAGGAGT           60

M  N  K  I  K  V  A  I  I  F  G  G  C  S  E  E  H  D            18
TTACAGCATGAATAAAATAAAAGTCGCAATTATCTTCGGCGGTTGCTCGGAGGAACATGA          120

V  S  V  K  S  A  I  E  I  A  A  N  I  N  T  E  K  F  D  P         38
TGTGTCGGTAAAATCCGCAATAGAAATTGCTGCGAACATTAATACTGAAAAATTCGATCC          180

H  Y  I  G  I  T  K  N  G  V  W  K  L  C  K  K  P  C  T  E         58
GCACTACATCGGAATTACAAAAAACGGCGTATGGAAGCTATGCAAGAAGCCATGTACGGA          240

W  E  A  D  S  L  P  A  I  F  S  P  D  R  K  T  H  G  L  L         78
ATGGGAAGCCGATAGTCTCCCCGCCATATTCTCCCCGGATAGGAAAACGCATGGTCTGCT          300
    primer 1
   V  M  K  E  R  E  Y  E  T  R  R  I  D  V  A  F  P  V  L  H         98
TGTCATGAAAGAAAGAGAATACGAAACTCGGCGTATTGACGTGGCTTTCCCGGTTTTGCA          360

G  K  C  G  E  D  G  A  I  Q  G  L  F  E  L  S  G  I  P  Y        118
TGGCAAATGCGGGGAGGATGGTGCGATACAGGGTCTGTTTGAATTGTCTGGTATCCCCTA          420

V  G  C  D  I  Q  S  S  A  A  C  M  D  K  S  L  A  Y  I  L        138
TGTAGGCTGCGATATTCAAAGCTCCGCAGCTTGCATGGACAAATCACTGGCCTACATTCT          480

T  K  N  A  G  I  A  V  P  E  F  Q  M  I  E  K  G  D  K  P        158
TACAAAAAATGCGGGCATCGCCGTCCCCGAATTTCAAATGATTGAAAAAGGTGACAAACC          540

E  A  R  T  L  T  Y  P  V  F  V  K  P  A  R  S  G  S  S  F        178
GGAGGCGAGGACGCTTACCTACCCTGTCTTTGTGAAGCCGGCACGGTCAGGTTCGTCCTT          600
```

*FIG. 1A*

```
     G   V   T   K   V   N   S   T   E   E   L   N   A   A   I   E   A   A   G   Q       198
TGGCGTAACCAAAGTAAACAGTACGGAAGAACTAAACGCTGCGATAGAAGCAGCAGGACA                              660

Y   D   G   K   I   L   I   E   Q   A   I   S   G   C   E   V   G   C   A   V       218
ATATGATGGAAAAATCTTAATTGAGCAAGCGATTTCGGGCTGTGAGGTCGGCTGCGCGGT                              720

M   G   N   E   D   D   L   I   V   G   E   V   D   Q   I   R   L   S   H   G       238
CATGGGAAACGAGGATGATTTGATTGTCGGCGAAGTGGATCAAATCCGGTTGAGCCACGG                              780

I   F   R   I   H   Q   E   N   E   P   E   K   G   S   E   N   A   M   I   I       258
TATCTTCCGCATCCATCAGGAAAACGAGCCGGAAAAAGGCTCAGAGAATGCGATGATTAT                              840

V   P   A   D   I   P   V   E   E   R   N   R   V   Q   E   T   A   K   K   V       278
CGTTCCAGCAGACATTCCGGTCGAGGAACGAAATCGGGTGCAAGAAACGGCAAAGAAAGT                              900
                         primer 2
     Y   R   V   L   G   C   R   G   L   A   R   V   D   L   F   L   Q   E   D   G       298
ATATCGGGTGCTTGGATGCAGAGGGCTTGCTCGTGTTGATCTTTTTTTGCAGGAGGATGG                              960

G   I   V   L   N   E   V   N   T   L   P   G   F   T   S   Y   S   R   Y   P       318
CGGCATCGTTCTAAACGAGGTCAATACCCTGCCCGGTTTTACATCGTACAGCCGCTATCC                             1020

R   M   A   A   A   A   G   I   T   L   P   A   L   I   D   S   L   I   T   L       338
ACGCATGGCGGCTGCCGCAGGAATCACGCTTCCCGCACTAATTGACAGCCTGATTACATT                             1080

A   I   E   R   *                                                                    342
GGCGATAGAGAGGTGACCCGTATGGAAAATGGTTTTTTGTTTTTTAGATGAAATGTTGCA                             1140 amorce 1:  5' ATGGGAAGCCGATAGTC 3'   pos. 241-258 amorce 2:  5' GATTTCGTTCCTCGACC 3'   pos. 860-877 (reverse-complementary)
```

*FIG. 1B*

```
         domain 1
VanA    MNRIKVAILF  GGCSEEHDVS  VKSAIEIAAN  INKEKYEPLY  IGITKSGVWK  MCEKPCAEWE  NDNCYSAVLS  PDKKMHGLLV  KKNHEYEIN-  ------HVD   92
VanB    MNKIKVAIIF  GGCSEEHDVS  VKSAIEIAAN  INTEKFDPHY  IGITKNGVWK  LCKKPCTEWE  AD-SLPAIFS  PDRKTHGLLV  MKEREYETR-  ------RID   91
VanC    --MKKIAVLF  GGNSPEYSVS  LISAASVIQA  IDPLKYEVMT  IGIAPTMDWY  WYQGNLANVR  NDTWLEDHKN  CHQLIFSSQG  FILGEKRI--  ------VPD   89
EFDd1   ---LKIILLY  GGRSEEHDVS  VLSAYSVLNA  IYYKYYQVQL  VFISKDGQWV  KGPLLSERPQ  NKEVLHLIWA  QTPEETGEFS  GKRISPSEIY  E------EEA  91
EcDdlA  MEKLRVGIVF  GGKSAEHEVS  LQSAKNIVDA  IDKSRFDVVL  LGIDKQGQWH  VSDASNYLLN  ADDPAHIALR  PSATSLAQVP  GKHEHQLIDA  QNGQPLPTVD 100
StDdlA  MAKLRVGIVF  GGKSAEHEVS  LQSAKNIVDA  IDKTRFDVVL  LGIDKAGQWH  VNDAENYLQN  ADDPAHIALR  PSAISLAQVP  GKHQHQLINA  QNGQPLPTVD 100
EcDdlB  -MTDKIAVLL  GGTSAEREVS  LNSGAAVLAG  LREGGIDAYP  VDPKEVDVTQ  LKSM------  ----------  ----------  ----------  ------GFQ   56

CC CCC      IIII II     CI IC C                                         CC                                III IC I
        I CII       IIII CIICC  CI  II      CI   CIII        C      IC       ICCCII domain 2
VanA    VAFSALHGKS  GEDGSIQGLF  ELSGIPFVGC  DIQSSAICMD  KSLTYIVAKN  AGIATPAFWV  INKDDR----  -----PVAAT  FTYPVFVKPA  RSGSSFGVKK 183
VanB    VAFPVLHGKC  GEDGAIQGLF  ELSGIPYVGC  DIQSSAACMD  KSLAYILTKN  AGIAVPEFQM  IEKGDK----  -----PEART  LTYPVFVKPA  RSGSSFGVTK 182
VanC    VLFPVLHGKY  GEDGCIQGLL  ELMNLPYVGC  HVAASALCMN  KWLLHQLADT  MGIASAPTLL  LSRYENDPAT  ID--RFIQD   HGFPIFIKPN  EAGSSKGITK 186
EFDd1   IVFPVLHGPN  GEDGSIQGFM  ETINMPYVGA  GVLASANAMD  KIMIKVLLQI  VGIPQVPFVP  VLRSDWKGNP  KEVTEKCEGS  LIYPVFVKPA  NMGSSVGISK 191
EcDdlA  VIFPIVHGTL  GEDGSLQGML  RVANLPFVGS  DVLASAACMD  KDVIKRLLRD  AGLNIAPFIT  LIRANRHNIS  FA---EVESK  LGLPLFVKPA  NQGSSVGVSK 197
StDdlA  VIFPIVHGTL  GEDGSLQGML  RVANLPFVGS  DVLSSAACMD  KDVAKRLLRD  AGLNIAPFIT  LIRTNRHAFS  FA---EVESR  LGLPLFVKPA  NQGSSVGVSK 197
EcDdlB  KVFIALHGRG  GEDGTLQGML  ELMGLPYTGS  GVMASALSMD  KLRSKLLWQG  AGLPVAPWVA  LIRAEFEKGL  SDKQLAEISA  LGLPVIVKPS  REGSSVGMSK 156

C          IC         I          CC
```

FIG. 2A

```
VanA    VNSADELDYA  IESARQYDSK  ILIEQAVSGC  EVGCAVLGNS  AALVWGEVDQ  IRLQYGIFRI  HQEVEPEKGS  ENAVITVPAD  LSAEERGRIQ  ETAKKIYKAL  283
VanB    VNSTEELNAA  IEAAGQYDGK  ILIEQAISGC  EVGCAVMGNE  DDLIVGEVDQ  IRLSHGIFRI  HQENEPEKGS  ENAMIIVPAD  IPVEERNRVQ  ETAKKVYRVL  282
VanC    VTDKTALQSA  LTTAFAYGST  VLIQKAIAGI  EIGCGILGNE  -QLIIGACDA  ISLVDGFFDF  EEKYQLIS--  --ATIIVPAP  LPLALESQIK  EQAQLLYRNL  281
EfDdl   VENRDELQEA  LEEAFRYDAR  AIVEQGIEAR  EIEVAILGNE  -DVRTILPGE  VVKDVAFYDY  DAKYINNT--  --IEMQIPAH  VPEEVAHQAQ  EYAKKAYIML  286
EcDdlA  VTSEEQYAIA  VDLAFEFDHK  VIVEQGIKGR  EIECAVLGND  -NPQASTCGE  IVLTSDFYAY  DIKYIDEDG-  --AKVVVPAA  IAPEINDKIR  AIAVQAYQIL  293
StDdlA  VANEAQYQQA  VALAFEFDHK  VVVEQGIKGR  EIECAVLGND  -NPQASTCGE  IVLNSEFYAY  DIKYIDDNG-  --AQVVVPAQ  IPSEVNDKIR  AIAIQAYQIL  293
EcDdlB  VVAENALQDA  LRLAFQHDEE  VLIEKWLSGP  EFTVAILGEE  ----ILPSIR  IQPSGTFYDY  EAKYLSDE--  --IQYFCPAG  LEASQEANLQ  ALVLKAWTIL  248
         I  IC        C    I       C  CC  CCC I       IC  CC C       C     C         C  C                   II  C         I
                              domain 3

VanA    GCRGLARVDM  FLQDNGRIVL  NEVNTILPGFT SYSRYPRMMA  AAGIALPELI  DRLIVLALKG  --          -           343
VanB    GCRGLARVDL  FLQEDGGIVL  NEVNTILPGFT SYSRYPRMAA  AAGITLPALI  DSLITLAIER  --          -           342
VanC    GLTGLARIDF  FVTNQGAIYL  NEINTMPGFT  GHSRYPAMMA  EVGLSYEILV  EQLIALAEED  KR-         -           343
EfDdl   DGSGLSRCDF  FLTSKNELFL  NELNTMPGFT  PFSMYPLLWE  NMGLKYSDLI  EELIQLALNR  FK-         -           348
EcDdlA  GCAGMARVDV  FLTPENEVVI  NEINTILPGFT ASGLGYTDLI  TRLIELALER  HAANNALKIT              M           364
StDdlA  GCAGMARVDV  FLTADNEVVI  NEINTILPGFT ASGLGYTDLI  SRLIELALER  HIANNALKIT              M           364
EcDdlB  GCKGWGRIDV  MLDSDGQFYL  LEANTSPGMT  SHSLVPMAAR  QAGMSFSQLV  VRILELAD--  --          -           306
         I  II IICI    CC   C      C   III IICI   I    IC   IC    CC II
                              domain 4
```

FIG. 2B

```
                        RBS           L  K  I  I  L  L  Y  G  G  R    10
AAAGACAGGAAAGAAACTAGGAGGACAAGCATTTGAAGATTATTTTGTTGTATGGCGGCA          60

S  E  E  H  D  V  S  V  L  S  A  Y  S  V  L  N  A  I  Y  Y         30
GAAGTGAAGAGCACGATGTGTCTGTTTTGTCTGCATATTCCGTTTTAAATGCAATCTATT         120

K  Y  Y  Q  V  Q  L  V  F  I  S  K  D  G  Q  W  V  K  G  P         50
ATAAATATTATCAAGTACAGTTAGTCTTTATTAGTAAAGACGGTCAATGGGTAAAAGGCC         180

L  L  S  E  R  P  Q  N  K  E  V  L  H  L  T  W  A  Q  T  P         70
CTCTTTTATCTGAACGACCACAAAATAAAGAAGTTTTACATTTAACTTGGGCACAAACAC        240

E  E  T  G  E  F  S  G  K  R  I  S  P  S  E  I  Y  E  E  E         90
CTGAAGAAACAGGCGAATTTTCAGGAAAACGAATCAGTCCTTCGGAAATTTATGAAGAAG        300

A  I  V  F  P  V  L  H  G  P  N  G  E  D  G  T  I  Q  G  F        110
AAGCGATTGTTTTCCCTGTTTTACATGGGCCAAATGGTGAAGATGGAACAATTCAAGGAT        360

M  E  T  I  N  M  P  Y  V  G  A  G  V  L  A  S  V  N  A  M        130
TCATGGAAACCATTAATATGCCTTATGTAGGCGCGGGTGTCTTAGCTAGCGTTAACGCAA        420

D  K  I  M  T  K  Y  L  L  Q  T  V  G  I  P  Q  V  P  F  V        150
TGGACAAAATCATGACGAAATATCTTTTACAAACTGTTGGCATTCCACAAGTACCATTCG        480

P  V  L  R  S  D  W  K  G  N  P  K  E  V  F  E  K  C  E  G        170
TGCCAGTTTTAAGAAGTGACTGGAAAGGAAATCCAAAAGAAGTCTTTGAAAAATGTGAAG       540
```

*FIG. 4A*

```
    S   L   I   Y   P   V   F   V   K   P   A   N   M   G   S   S   V   G   I   S   190
GTTCTTTAATTTATCCGGTCTTTGTTAAACCTGCCAATATGGGTTCTAGTGTCGGAATTA                            600

K   V   E   N   R   E   E   L   Q   E   A   L   E   E   A   F   R   Y   D   A   210
GCAAAGTGGAAAATCGTGAAGAATTGCAAGAAGCATTGGAAGAAGCTTTCCGTTATGATG                            660

R   A   I   V   E   Q   G   I   E   A   R   E   I   E   V   A   I   L   G   N   230
CCCGAGCAATTGTTGAACAAGGGATCGAAGCACGTGAAATTGAAGTAGCCATTTTAGGAA                            720

E   D   V   R   T   T   L   P   G   E   V   V   K   D   V   A   F   Y   D   Y   250
ATGAAGATGTCCGTACGACTTTACCTGGTGAAGTGGTGAAAGATGTCGCTTTCTATGATT                            780

D   A   K   Y   I   N   N   T   I   E   M   Q   I   P   A   H   V   P   E   E   270
ATGATGCAAAATACATCAATAACACGATTGAAATGCAAATCCCAGCGCATGTTCCAGAAG                            840

V   A   H   Q   A   Q   E   Y   A   K   K   A   Y   I   M   L   D   G   S   G   290
AAGTAGCTCATCAAGCGCAAGAATACGCTAAAAAAGCGTATATTATGTTAGATGGAAGTG                            900

L   S   R   C   D   F   F   L   T   S   K   N   E   L   F   L   N   E   L   N   310
GCTTAAGTCGCTGTGATTTCTTCTTAACAAGCAAAAACGAATTATTCCTGAATGAATTGA                            960

T   M   P   G   F   T   D   F   S   M   Y   P   L   L   W   E   N   M   G   L   330
ACACCATGCCTGGTTTTACTGACTTTAGTATGTATCCTTTACTGTGGGAAAATATGGGCT                           1020

K   Y   S   D   L   I   E   E   L   I   Q   L   A   L   N   R   F   K   *        348
TGAAATACAGTGATTTAATTGAGGAACTGATTCAGTTAGCTTTGAATCGTTTTAAATAA                            1079
```

*FIG. 4B*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1140 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 68..1093

(xi) SEQUENCE DESCRIPTION: SEQ ID NO:1:

```
GAGCGTGTGC TGCGAGATAC CACAGAAAAC AATCAGAATT GTCTTAACTT TGAAAGGAGT          60

TTACAGC ATG AAT AAA ATA AAA GTC GCA ATT ATC TTC GGC GGT TGC TCG         109
        Met Asn Lys Ile Lys Val Ala Ile Ile Phe Gly Gly Cys Ser
          1               5                  10

GAG GAA CAT GAT GTG TCG GTA AAA TCC GCA ATA GAA ATT GCT GCG AAC         157
Glu Glu His Asp Val Ser Val Lys Ser Ala Ile Glu Ile Ala Ala Asn
 15                  20                  25                  30

ATT AAT ACT GAA AAA TTC GAT CCG CAC TAC ATC GGA ATT ACA AAA AAC         205
Ile Asn Thr Glu Lys Phe Asp Pro His Tyr Ile Gly Ile Thr Lys Asn
                 35                  40                  45

GGC GTA TGG AAG CTA TGC AAG AAG CCA TGT ACG GAA TGG GAA GCC GAT         253
Gly Val Trp Lys Leu Cys Lys Lys Pro Cys Thr Glu Trp Glu Ala Asp
             50                  55                  60

AGT CTC CCC GCC ATA TTC TCC CCG GAT AGG AAA ACG CAT GGT CTG CTT         301
Ser Leu Pro Ala Ile Phe Ser Pro Asp Arg Lys Thr His Gly Leu Leu
         65                  70                  75

GTC ATG AAA GAA AGA GAA TAC GAA ACT CGG CGT ATT GAC GTG GCT TTC         349
Val Met Lys Glu Arg Glu Tyr Glu Thr Arg Arg Ile Asp Val Ala Phe
     80                  85                  90

CCG GTT TTG CAT GGC AAA TGC GGG GAG GAT GGT GCG ATA CAG GGT CTG         397
Pro Val Leu His Gly Lys Cys Gly Glu Asp Gly Ala Ile Gln Gly Leu
```

```
    95                  100                 105                     110
TTT GAA TTG TCT GGT ATC CCC TAT GTA GGC TGC GAT ATT CAA AGC TCC            445
Phe Glu Leu Ser Gly Ile Pro Tyr Val Gly Cys Asp Ile Gln Ser Ser
                115                 120                 125

GCA GCT TGC ATG GAC AAA TCA CTG GCC TAC ATT CTT ACA AAA AAT GCG            493
Ala Ala Cys Met Asp Lys Ser Leu Ala Tyr Ile Leu Thr Lys Asn Ala
                130                 135                 140

GGC ATC GCC GTC CCC GAA TTT CAA ATG ATT GAA AAA GGT GAC AAA CCG            541
Gly Ile Ala Val Pro Glu Phe Gln Met Ile Glu Lys Gly Asp Lys Pro
                145                 150                 155

GAG GCG AGG ACG CTT ACC TAC CCT GTC TTT GTG AAG CCG GCA CGG TCA            589
Glu Ala Arg Thr Leu Thr Tyr Pro Val Phe Val Lys Pro Ala Arg Ser
            160                 165                 170

GGT TCG TCC TTT GGC GTA ACC AAA GTA AAC AGT ACG GAA GAA CTA AAC            637
Gly Ser Ser Phe Gly Val Thr Lys Val Asn Ser Thr Glu Glu Leu Asn
175                 180                 185                 190

GCT GCG ATA GAA GCA GCA GGA CAA TAT GAT GGA AAA ATC TTA ATT GAG            685
Ala Ala Ile Glu Ala Ala Gly Gln Tyr Asp Gly Lys Ile Leu Ile Glu
                195                 200                 205

CAA GCG ATT TCG GGC TGT GAG GTC GGC TGC GCG GTC ATG GGA AAC GAG            733
Gln Ala Ile Ser Gly Cys Glu Val Gly Cys Ala Val Met Gly Asn Glu
                210                 215                 220

GAT GAT TTG ATT GTC GGC GAA GTG GAT CAA ATC CGG TTG AGC CAC GGT            781
Asp Asp Leu Ile Val Gly Glu Val Asp Gln Ile Arg Leu Ser His Gly
            225                 230                 235

ATC TTC CGC ATC CAT CAG GAA AAC GAG CCG GAA AAA GGC TCA GAG AAT            829
Ile Phe Arg Ile His Gln Glu Asn Glu Pro Glu Lys Gly Ser Glu Asn
            240                 245                 250

GCG ATG ATT ATC GTT CCA GCA GAC ATT CCG GTC GAG GAA CGA AAT CGG            877
Ala Met Ile Ile Val Pro Ala Asp Ile Pro Val Glu Glu Arg Asn Arg
255                 260                 265                 270

GTG CAA GAA ACG GCA AAG AAA GTA TAT CGG GTG CTT GGA TGC AGA GGG            925
Val Gln Glu Thr Ala Lys Lys Val Tyr Arg Val Leu Gly Cys Arg Gly
                275                 280                 285

CTT GCT CGT GTT GAT CTT TTT TTG CAG GAG GAT GGC GGC ATC GTT CTA            973
Leu Ala Arg Val Asp Leu Phe Leu Gln Glu Asp Gly Gly Ile Val Leu
                290                 295                 300

AAC GAG GTC AAT ACC CTG CCC GGT TTT ACA TCG TAC AGC CGC TAT CCA           1021
Asn Glu Val Asn Thr Leu Pro Gly Phe Thr Ser Tyr Ser Arg Tyr Pro
            305                 310                 315

CGC ATG GCG GCT GCC GCA GGA ATC ACG CTT CCC GCA CTA ATT GAC AGC           1069
Arg Met Ala Ala Ala Ala Gly Ile Thr Leu Pro Ala Leu Ile Asp Ser
                320                 325                 330

CTG ATT ACA TTG GCG ATA GAG AGG TGACCCGTAT GGAAAATGGT TTTTTGTTTT          1123
Leu Ile Thr Leu Ala Ile Glu Arg
335                 340

TTAGATGAAA TGTTGCA                                                        1140

(2) INFORMATION FOR SEQ ID NO:2:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Lys Ile Lys Val Ala Ile Ile Phe Gly Gly Cys Ser Glu Glu
  1               5                  10                  15
```

```
His Asp Val Ser Val Lys Ser Ala Ile Glu Ile Ala Ala Asn Ile Asn
         20                  25                  30

Thr Glu Lys Phe Asp Pro His Tyr Ile Gly Ile Thr Lys Asn Gly Val
         35                  40                  45

Trp Lys Leu Cys Lys Lys Pro Cys Thr Glu Trp Glu Ala Asp Ser Leu
         50                  55                  60

Pro Ala Ile Phe Ser Pro Asp Arg Lys Thr His Gly Leu Leu Val Met
 65                  70                  75                  80

Lys Glu Arg Glu Tyr Glu Thr Arg Arg Ile Asp Val Ala Phe Pro Val
                 85                  90                  95

Leu His Gly Lys Cys Gly Glu Asp Gly Ala Ile Gln Gly Leu Phe Glu
                100                 105                 110

Leu Ser Gly Ile Pro Tyr Val Gly Cys Asp Ile Gln Ser Ser Ala Ala
            115                 120                 125

Cys Met Asp Lys Ser Leu Ala Tyr Ile Leu Thr Lys Asn Ala Gly Ile
130                 135                 140

Ala Val Pro Glu Phe Gln Met Ile Glu Lys Gly Asp Lys Pro Glu Ala
145                 150                 155                 160

Arg Thr Leu Thr Tyr Pro Val Phe Val Lys Pro Ala Arg Ser Gly Ser
                165                 170                 175

Ser Phe Gly Val Thr Lys Val Asn Ser Thr Glu Glu Leu Asn Ala Ala
            180                 185                 190

Ile Glu Ala Ala Gly Gln Tyr Asp Gly Lys Ile Leu Ile Glu Gln Ala
        195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Ile Val Pro Ala Asp Ile Pro Val Glu Glu Arg Asn Arg Val Gln
                260                 265                 270

Glu Thr Ala Lys Lys Val Tyr Arg Val Leu Gly Cys Arg Gly Leu Ala
            275                 280                 285

Arg Val Asp Leu Phe Leu Gln Glu Asp Gly Gly Ile Val Leu Asn Glu
        290                 295                 300

Val Asn Thr Leu Pro Gly Phe Thr Ser Tyr Ser Arg Tyr Pro Arg Met
305                 310                 315                 320

Ala Ala Ala Ala Gly Ile Thr Leu Pro Ala Leu Ile Asp Ser Leu Ile
                325                 330                 335

Thr Leu Ala Ile Glu Arg
            340
```

(2) INFORMATION FOR SEQ ID NO:3:

(i) SEQUENCE CHARACTERISTICS:
        (A) LENGTH: 589 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

```
TCTGTTTGAA TTGTCTGGTA TCCCCTATGT AGGCTGCGAT ATTCAAAGCT CCGCAGCTTG      60

CATGGACAAA TCACTGGCCT ACATTCTTAC AAAAAATGCG GGCATCGCCG TCCCCGAATT     120
```

```
TCAAATGATT GAAAAAGGTG ACAAACCGGA GGCGAGGACG CTTACCTACC CTGTCTTTGT      180

GAAGCCGGCA CGGTCAGGTT CGTCCTTTGG CGTAACCAAA GTAAACAGTA CGGAAGAACT      240

AAACGCTGCG ATAGAAGCAG CAGGACAATA TGATGGAAAA ATCTTAATTG AGCAAGCGAT      300

TTCGGGCTGT GAGGTCGGCT GCGCGGTCAT GGGAAACGAG GATGATTTGA TTGTCGGCGA      360

AGTGGATCAA ATCCGGTTGA GCCACGGTAT CTTCCGCATC CATCAGGAAA ACGAGCCGGA      420

AAAAGGCTCA GAGAATGCGA TGATTATCGT TCCAGCAGAC ATTCCGGTCG AGGAACGAAA      480

TCGGGTGCAA GAAACGGCAA AGAAAGTATA TCGGGTGCTT GGATGCAGAG GGCTTGCTCG      540

TGTTGATCTT TTTTTGCAGG AGGATGGCGG CATCGTTCTA AACGAGGTC                  589
```

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

```
ATGGGAAGCC GATAGTC                                                     17
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

```
GATTTCGTTC CTCGACC                                                     17
```

(2) INFORMATION FOR SEQ ID NO:6:

(i) SEQUENCE CHARACTERISTICS:
        (A) LENGTH: 343 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

```
Met Asn Arg Ile Lys Val Ala Ile Leu Phe Gly Gly Cys Ser Glu Glu
1               5                   10                  15

His Asp Val Ser Val Lys Ser Ala Ile Glu Ile Ala Ala Asn Ile Asn
                20                  25                  30

Lys Glu Lys Tyr Glu Pro Leu Tyr Ile Gly Ile Thr Lys Ser Gly Val
            35                  40                  45

Trp Lys Met Cys Glu Lys Pro Cys Ala Glu Trp Glu Asn Asp Asn Cys
        50                  55                  60

Tyr Ser Ala Val Leu Ser Pro Asp Lys Lys Met His Gly Leu Leu Val
65                  70                  75                  80

Lys Lys Asn His Glu Tyr Glu Ile Asn His Val Asp Val Ala Phe Ser
                85                  90                  95

Ala Leu His Gly Lys Ser Gly Glu Asp Gly Ser Ile Gln Gly Leu Phe
```

-continued

```
                100                 105                 110
Glu Leu Ser Gly Ile Pro Phe Val Gly Cys Asp Ile Gln Ser Ser Ala
            115                 120                 125
Ile Cys Met Asp Lys Ser Leu Thr Tyr Ile Val Ala Lys Asn Ala Gly
130                 135                 140
Ile Ala Thr Pro Ala Phe Trp Val Ile Asn Lys Asp Asp Arg Pro Val
145                 150                 155                 160
Ala Ala Thr Phe Thr Tyr Pro Val Phe Val Lys Pro Ala Arg Ser Gly
                165                 170                 175
Ser Ser Phe Gly Val Lys Lys Val Asn Ser Ala Asp Glu Leu Asp Tyr
            180                 185                 190
Ala Ile Glu Ser Ala Arg Gln Tyr Asp Ser Lys Ile Leu Ile Glu Gln
            195                 200                 205
Ala Val Ser Gly Cys Glu Val Gly Cys Ala Val Leu Gly Asn Ser Ala
            210                 215                 220
Ala Leu Val Val Gly Glu Val Asp Gln Ile Arg Leu Gln Tyr Gly Ile
225                 230                 235                 240
Phe Arg Ile His Gln Glu Val Glu Pro Glu Lys Gly Ser Glu Asn Ala
                245                 250                 255
Val Ile Thr Val Pro Ala Asp Leu Ser Ala Glu Glu Arg Gly Arg Ile
                260                 265                 270
Gln Glu Thr Ala Lys Lys Ile Tyr Lys Ala Leu Gly Cys Arg Gly Leu
            275                 280                 285
Ala Arg Val Asp Met Phe Leu Gln Asp Asn Gly Arg Ile Val Leu Asn
            290                 295                 300
Glu Val Asn Thr Leu Pro Gly Phe Thr Ser Tyr Ser Arg Tyr Pro Arg
305                 310                 315                 320
Met Met Ala Ala Ala Gly Ile Ala Leu Pro Glu Leu Ile Asp Arg Leu
                325                 330                 335
Ile Val Leu Ala Leu Lys Gly
                340

(2) INFORMATION FOR SEQ ID NO:7:

(i) SEQUENCE CHARACTERISTICS:
        (A) LENGTH: 343 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:7:

Met Lys Lys Ile Ala Val Leu Phe Gly Gly Asn Ser Pro Glu Tyr Ser
1               5                   10                  15
Val Ser Leu Thr Ser Ala Ala Ser Val Ile Gln Ala Ile Asp Pro Leu
                20                  25                  30
Lys Tyr Glu Val Met Thr Ile Gly Ile Ala Pro Thr Met Asp Trp Tyr
            35                  40                  45
Trp Tyr Gln Gly Asn Leu Ala Asn Val Arg Asn Asp Thr Trp Leu Glu
        50                  55                  60
Asp His Lys Asn Cys His Gln Leu Thr Phe Ser Ser Gln Gly Phe Ile
65                  70                  75                  80
Leu Gly Glu Lys Arg Ile Val Pro Asp Val Leu Phe Pro Val Leu His
                85                  90                  95
Gly Lys Tyr Gly Glu Asp Gly Cys Ile Gln Gly Leu Leu Glu Leu Met
```

-continued

```
                100                 105                 110
Asn Leu Pro Tyr Val Gly Cys His Val Ala Ser Ala Leu Cys Met
            115                 120                 125
Asn Lys Trp Leu Leu His Gln Leu Ala Asp Thr Met Gly Ile Ala Ser
130                 135                 140
Ala Pro Thr Leu Leu Leu Ser Arg Tyr Glu Asn Asp Pro Ala Thr Ile
145                 150                 155                 160
Asp Arg Phe Ile Gln Asp His Gly Phe Pro Ile Phe Ile Lys Pro Asn
                165                 170                 175
Glu Ala Gly Ser Ser Lys Gly Ile Thr Lys Val Thr Asp Lys Thr Ala
                180                 185                 190
Leu Gln Ser Ala Leu Thr Thr Ala Phe Ala Tyr Gly Ser Thr Val Leu
                195                 200                 205
Ile Gln Lys Ala Ile Ala Gly Ile Glu Ile Gly Cys Gly Ile Leu Gly
            210                 215                 220
Asn Glu Gln Leu Thr Ile Gly Ala Cys Asp Ala Ile Ser Leu Val Asp
225                 230                 235                 240
Gly Phe Phe Asp Phe Glu Glu Lys Tyr Gln Leu Ile Ser Ala Thr Ile
                245                 250                 255
Thr Val Pro Ala Pro Leu Pro Leu Ala Leu Glu Ser Gln Ile Lys Glu
                260                 265                 270
Gln Ala Gln Leu Leu Tyr Arg Asn Leu Gly Leu Thr Gly Leu Ala Arg
                275                 280                 285
Ile Asp Phe Phe Val Thr Asn Gln Gly Ala Ile Tyr Leu Asn Glu Ile
            290                 295                 300
Asn Thr Met Pro Gly Phe Thr Gly His Ser Arg Tyr Pro Ala Met Met
305                 310                 315                 320
Ala Glu Val Gly Leu Ser Tyr Glu Ile Leu Val Glu Gln Leu Ile Ala
                325                 330                 335
Leu Ala Glu Glu Asp Lys Arg
            340

(2) INFORMATION FOR SEQ ID NO:8:

(i) SEQUENCE CHARACTERISTICS:
        (A) LENGTH: 348 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

Leu Lys Ile Ile Leu Tyr Gly Gly Arg Ser Glu Glu His Asp Val
1               5                   10                  15
Ser Val Leu Ser Ala Tyr Ser Val Leu Asn Ala Ile Tyr Tyr Lys Tyr
                20                  25                  30
Tyr Gln Val Gln Leu Val Phe Ile Ser Lys Asp Gly Gln Trp Val Lys
            35                  40                  45
Gly Pro Leu Leu Ser Glu Arg Pro Gln Asn Lys Glu Val Leu His Leu
50                  55                  60
Thr Trp Ala Gln Thr Pro Glu Glu Thr Gly Phe Ser Gly Lys Arg
65                  70                  75                  80
Ile Ser Pro Ser Glu Ile Tyr Glu Glu Ala Ile Val Phe Pro Val
                85                  90                  95
Leu His Gly Pro Asn Gly Glu Asp Gly Ser Ile Gln Gly Phe Met Glu
```

-continued

```
                100                 105                 110
Thr Ile Asn Met Pro Tyr Val Gly Ala Gly Val Leu Ala Ser Ala Asn
            115                 120                 125
Ala Met Asp Lys Ile Met Thr Lys Val Leu Leu Gln Thr Val Gly Ile
130                 135                 140
Pro Gln Val Pro Phe Val Pro Val Leu Arg Ser Asp Trp Lys Gly Asn
145                 150                 155                 160
Pro Lys Glu Val Thr Glu Lys Cys Glu Gly Ser Leu Ile Tyr Pro Val
                165                 170                 175
Phe Val Lys Pro Ala Asn Met Gly Ser Ser Val Gly Ile Ser Lys Val
            180                 185                 190
Glu Asn Arg Asp Glu Leu Gln Glu Ala Leu Glu Glu Ala Phe Arg Tyr
            195                 200                 205
Asp Ala Arg Ala Ile Val Glu Gln Gly Ile Glu Ala Arg Glu Ile Glu
210                 215                 220
Val Ala Ile Leu Gly Asn Glu Asp Val Arg Thr Thr Leu Pro Gly Glu
225                 230                 235                 240
Val Val Lys Asp Val Ala Phe Tyr Asp Tyr Asp Ala Lys Tyr Ile Asn
                245                 250                 255
Asn Thr Ile Glu Met Gln Ile Pro Ala His Val Pro Glu Glu Val Ala
            260                 265                 270
His Gln Ala Gln Glu Tyr Ala Lys Lys Ala Tyr Ile Met Leu Asp Gly
            275                 280                 285
Ser Gly Leu Ser Arg Cys Asp Phe Phe Leu Thr Ser Lys Asn Glu Leu
        290                 295                 300
Phe Leu Asn Glu Leu Asn Thr Met Pro Gly Phe Thr Pro Phe Ser Met
305                 310                 315                 320
Tyr Pro Leu Leu Trp Glu Asn Met Gly Leu Lys Tyr Ser Asp Leu Ile
                325                 330                 335
Glu Glu Leu Ile Gln Leu Ala Leu Asn Arg Phe Lys
            340                 345

(2) INFORMATION FOR SEQ ID NO:9:

(i) SEQUENCE CHARACTERISTICS:
        (A) LENGTH: 364 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

Met Glu Lys Leu Arg Val Gly Ile Val Phe Gly Gly Lys Ser Ala Glu
1               5                   10                  15
His Glu Val Ser Leu Gln Ser Ala Lys Asn Ile Val Asp Ala Ile Asp
            20                  25                  30
Lys Ser Arg Phe Asp Val Val Leu Leu Gly Ile Asp Lys Gln Gly Gln
        35                  40                  45
Trp His Val Ser Asp Ala Ser Asn Tyr Leu Leu Asn Ala Asp Asp Pro
    50                  55                  60
Ala His Ile Ala Leu Arg Pro Ser Ala Thr Ser Leu Ala Gln Val Pro
65                  70                  75                  80
Gly Lys His Glu His Gln Leu Ile Asp Ala Gln Asn Gly Gln Pro Leu
                85                  90                  95
Pro Thr Val Asp Val Ile Phe Pro Ile Val His Gly Thr Leu Gly Glu
```

-continued

```
                100                 105                 110
Asp Gly Ser Leu Gln Gly Met Leu Arg Val Ala Asn Leu Pro Phe Val
            115                 120                 125
Gly Ser Asp Val Leu Ala Ser Ala Ala Cys Met Asp Lys Asp Val Thr
130                 135                 140
Lys Arg Leu Leu Arg Asp Ala Gly Leu Asn Ile Ala Pro Phe Ile Thr
145                 150                 155                 160
Leu Thr Arg Ala Asn Arg His Asn Ile Ser Phe Ala Glu Val Glu Ser
                165                 170                 175
Lys Leu Gly Leu Pro Leu Phe Val Lys Pro Ala Asn Gln Gly Ser Ser
            180                 185                 190
Val Gly Val Ser Lys Val Thr Ser Glu Glu Gln Tyr Ala Ile Ala Val
            195                 200                 205
Asp Leu Ala Phe Glu Phe Asp His Lys Val Ile Val Glu Gln Gly Ile
            210                 215                 220
Lys Gly Arg Glu Ile Glu Cys Ala Val Leu Gly Asn Asp Asn Pro Gln
225                 230                 235                 240
Ala Ser Thr Cys Gly Glu Ile Val Leu Thr Ser Asp Phe Tyr Ala Tyr
                245                 250                 255
Asp Thr Lys Tyr Ile Asp Glu Asp Gly Ala Lys Val Val Val Pro Ala
            260                 265                 270
Ala Ile Ala Pro Glu Ile Asn Asp Lys Ile Arg Ala Ile Ala Val Gln
            275                 280                 285
Ala Tyr Gln Thr Leu Gly Cys Ala Gly Met Ala Arg Val Asp Val Phe
            290                 295                 300
Leu Thr Pro Glu Asn Glu Val Val Ile Asn Glu Ile Asn Thr Leu Pro
305                 310                 315                 320
Gly Phe Thr Asn Ile Ser Met Tyr Pro Lys Leu Trp Gln Ala Ser Gly
                325                 330                 335
Leu Gly Tyr Thr Asp Leu Ile Thr Arg Leu Ile Glu Leu Ala Leu Glu
            340                 345                 350
Arg His Ala Ala Asn Asn Ala Leu Lys Thr Thr Met
            355                 360
```

(2) INFORMATION FOR SEQ ID NO:10:

(i) SEQUENCE CHARACTERISTICS:
        (A) LENGTH: 364 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

```
Met Ala Lys Leu Arg Val Gly Ile Val Phe Gly Gly Lys Ser Ala Glu
1               5                   10                  15
His Glu Val Ser Leu Gln Ser Ala Lys Asn Ile Val Asp Ala Ile Asp
                20                  25                  30
Lys Thr Arg Phe Asp Val Val Leu Leu Gly Ile Asp Lys Ala Gly Gln
            35                  40                  45
Trp His Val Asn Asp Ala Glu Asn Tyr Leu Gln Asn Ala Asp Asp Pro
        50                  55                  60
Ala His Ile Ala Leu Arg Pro Ser Ala Ile Ser Leu Ala Gln Val Pro
65                  70                  75                  80
Gly Lys His Gln His Gln Leu Ile Asn Ala Gln Asn Gly Gln Pro Leu
```

```
                            85                  90                      95
Pro Thr Val Asp Val Ile Phe Pro Ile Val His Gly Thr Leu Gly Glu
                100                 105                 110

Asp Gly Ser Leu Gln Gly Met Leu Arg Val Ala Asn Leu Pro Phe Val
            115                 120                 125

Gly Ser Asp Val Leu Ser Ser Ala Ala Cys Met Asp Lys Asp Val Ala
        130                 135                 140

Lys Arg Leu Leu Arg Asp Ala Gly Leu Asn Ile Ala Pro Phe Ile Thr
145                 150                 155                 160

Leu Thr Arg Thr Asn Arg His Ala Phe Ser Phe Ala Glu Val Glu Ser
                165                 170                 175

Arg Leu Gly Leu Pro Leu Phe Val Lys Pro Ala Asn Gln Gly Ser Ser
            180                 185                 190

Val Gly Val Ser Lys Val Ala Asn Glu Ala Gln Tyr Gln Gln Ala Val
        195                 200                 205

Ala Leu Ala Phe Glu Phe Asp His Lys Val Val Glu Gln Gly Ile
    210                 215                 220

Lys Gly Arg Glu Ile Glu Cys Ala Val Leu Gly Asn Asp Asn Pro Gln
225                 230                 235                 240

Ala Ser Thr Cys Gly Glu Ile Val Leu Asn Ser Glu Phe Tyr Ala Tyr
                245                 250                 255

Asp Thr Lys Tyr Ile Asp Asp Asn Gly Ala Gln Val Val Val Pro Ala
            260                 265                 270

Gln Ile Pro Ser Glu Val Asn Asp Lys Ile Arg Ala Ile Ala Ile Gln
        275                 280                 285

Ala Tyr Gln Thr Leu Gly Cys Ala Gly Met Ala Arg Val Asp Val Phe
    290                 295                 300

Leu Thr Ala Asp Asn Glu Val Val Ile Asn Glu Ile Asn Thr Leu Pro
305                 310                 315                 320

Gly Phe Thr Asn Ile Ser Met Tyr Pro Lys Leu Trp Gln Ala Ser Gly
                325                 330                 335

Leu Gly Tyr Thr Asp Leu Ile Ser Arg Leu Ile Glu Leu Ala Leu Glu
            340                 345                 350

Arg His Thr Ala Asn Asn Ala Leu Lys Thr Thr Met
        355                 360

(2) INFORMATION FOR SEQ ID NO:11:

(i) SEQUENCE CHARACTERISTICS:
        (A) LENGTH: 306 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

Met Thr Asp Lys Ile Ala Val Leu Leu Gly Gly Thr Ser Ala Glu Arg
1               5                   10                  15

Glu Val Ser Leu Asn Ser Gly Ala Ala Val Leu Ala Gly Leu Arg Glu
            20                  25                  30

Gly Gly Ile Asp Ala Tyr Pro Val Asp Pro Lys Glu Val Asp Val Thr
        35                  40                  45

Gln Leu Lys Ser Met Gly Phe Gln Lys Val Phe Ile Ala Leu His Gly
    50                  55                  60

Arg Gly Gly Glu Asp Gly Thr Leu Gln Gly Met Leu Glu Leu Met Gly
```

```
65                  70                  75                  80
Leu Pro Tyr Thr Gly Ser Gly Val Met Ala Ser Ala Leu Ser Met Asp
                85                  90                  95
Lys Leu Arg Ser Lys Leu Leu Trp Gln Gly Ala Gly Leu Pro Val Ala
                100                 105                 110
Pro Trp Val Ala Leu Thr Arg Ala Glu Phe Glu Lys Gly Leu Ser Asp
                115                 120                 125
Lys Gln Leu Ala Glu Ile Ser Ala Leu Gly Leu Pro Val Ile Val Lys
                130                 135                 140
Pro Ser Arg Glu Gly Ser Ser Val Gly Met Ser Lys Val Val Ala Glu
145                 150                 155                 160
Asn Ala Leu Gln Asp Ala Leu Arg Leu Ala Phe Gln His Asp Glu Glu
                165                 170                 175
Val Leu Ile Glu Lys Trp Leu Ser Gly Pro Glu Phe Thr Val Ala Ile
                180                 185                 190
Leu Gly Glu Glu Ile Leu Pro Ser Ile Arg Ile Gln Pro Ser Gly Thr
                195                 200                 205
Phe Tyr Asp Tyr Glu Ala Lys Tyr Leu Ser Asp Glu Thr Gln Tyr Phe
                210                 215                 220
Cys Pro Ala Gly Leu Glu Ala Ser Gln Glu Ala Asn Leu Gln Ala Leu
225                 230                 235                 240
Val Leu Lys Ala Trp Thr Thr Leu Gly Cys Lys Gly Trp Gly Arg Ile
                245                 250                 255
Asp Val Met Leu Asp Ser Asp Gly Gln Phe Tyr Leu Leu Glu Ala Asn
                260                 265                 270
Thr Ser Pro Gly Met Thr Ser His Ser Leu Val Pro Met Ala Ala Arg
                275                 280                 285
Gln Ala Gly Met Ser Phe Ser Gln Leu Val Val Arg Ile Leu Glu Leu
                290                 295                 300
Ala Asp
305

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

GGNGARGAYG GNWSNYTNCA RGGN                                           24

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

AAYACNHTNC CNGGNTTTAC N                                              21

(2) INFORMATION FOR SEQ ID NO:14:
```

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:14:

```
GGNGARGAYG GNRSNHTNCA RGG                                              23
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

```
TGRAANCCNG GNADNGTRTT                                                  20
```

(2) INFORMATION FOR SEQ ID NO:16:

(i) SEQUENCE CHARACTERISTICS:
        (A) LENGTH: 1079 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 33..1076

(xi) SEQUENCE DESCRIPTION: SEQ ID NO:16:

```
AAAGACAGGA AAGAAACTAG GAGGACAAGC AT TTG AAG ATT ATT TTG TTG TAT         53
                                   Leu Lys Ile Ile Leu Leu Tyr
                                                345

GGC GGC AGA AGT GAA GAG CAC GAT GTG TCT GTT TTG TCT GCA TAT TCC        101
Gly Gly Arg Ser Glu Glu His Asp Val Ser Val Leu Ser Ala Tyr Ser
350             355                 360                 365

GTT TTA AAT GCA ATC TAT TAT AAA TAT TAT CAA GTA CAG TTA GTC TTT        149
Val Leu Asn Ala Ile Tyr Tyr Lys Tyr Tyr Gln Val Gln Leu Val Phe
                370                 375                 380

ATT AGT AAA GAC GGT CAA TGG GTA AAA GGC CCT CTT TTA TCT GAA CGA        197
Ile Ser Lys Asp Gly Gln Trp Val Lys Gly Pro Leu Leu Ser Glu Arg
            385                 390                 395

CCA CAA AAT AAA GAA GTT TTA CAT TTA ACT TGG GCA CAA ACA CCT GAA        245
Pro Gln Asn Lys Glu Val Leu His Leu Thr Trp Ala Gln Thr Pro Glu
        400                 405                 410

GAA ACA GGC GAA TTT TCA GGA AAA CGA ATC AGT CCT TCG GAA ATT TAT        293
Glu Thr Gly Glu Phe Ser Gly Lys Arg Ile Ser Pro Ser Glu Ile Tyr
    415                 420                 425

GAA GAA GAA GCG ATT GTT TTC CCT GTT TTA CAT GGG CCA AAT GGT GAA        341
Glu Glu Glu Ala Ile Val Phe Pro Val Leu His Gly Pro Asn Gly Glu
430                 435                 440                 445

GAT GGA ACA ATT CAA GGA TTC ATG GAA ACC ATT AAT ATG CCT TAT GTA        389
Asp Gly Thr Ile Gln Gly Phe Met Glu Thr Ile Asn Met Pro Tyr Val
                450                 455                 460

GGC GCG GGT GTC TTA GCT AGC GTT AAC GCA ATG GAC AAA ATC ATG ACG        437
Gly Ala Gly Val Leu Ala Ser Val Asn Ala Met Asp Lys Ile Met Thr
```

```
                    465                 470                 475
AAA TAT CTT TTA CAA ACT GTT GGC ATT CCA CAA GTA CCA TTC GTG CCA       485
Lys Tyr Leu Leu Gln Thr Val Gly Ile Pro Gln Val Pro Phe Val Pro
            480                 485                 490

GTT TTA AGA AGT GAC TGG AAA GGA AAT CCA AAA GAA GTC TTT GAA AAA       533
Val Leu Arg Ser Asp Trp Lys Gly Asn Pro Lys Glu Val Phe Glu Lys
            495                 500                 505

TGT GAA GGT TCT TTA ATT TAT CCG GTC TTT GTT AAA CCT GCC AAT ATG       581
Cys Glu Gly Ser Leu Ile Tyr Pro Val Phe Val Lys Pro Ala Asn Met
510                 515                 520                 525

GGT TCT AGT GTC GGA ATT AGC AAA GTG GAA AAT CGT GAA GAA TTG CAA       629
Gly Ser Ser Val Gly Ile Ser Lys Val Glu Asn Arg Glu Glu Leu Gln
                530                 535                 540

GAA GCA TTG GAA GAA GCT TTC CGT TAT GAT GCC CGA GCA ATT GTT GAA       677
Glu Ala Leu Glu Glu Ala Phe Arg Tyr Asp Ala Arg Ala Ile Val Glu
            545                 550                 555

CAA GGG ATC GAA GCA CGT GAA ATT GAA GTA GCC ATT TTA GGA AAT GAA       725
Gln Gly Ile Glu Ala Arg Glu Ile Glu Val Ala Ile Leu Gly Asn Glu
            560                 565                 570

GAT GTC CGT ACG ACT TTA CCT GGT GAA GTG GTG AAA GAT GTC GCT TTC       773
Asp Val Arg Thr Thr Leu Pro Gly Glu Val Val Lys Asp Val Ala Phe
575                 580                 585

TAT GAT TAT GAT GCA AAA TAC ATC AAT AAC ACG ATT GAA ATG CAA ATC       821
Tyr Asp Tyr Asp Ala Lys Tyr Ile Asn Asn Thr Ile Glu Met Gln Ile
590                 595                 600                 605

CCA GCG CAT GTT CCA GAA GAA GTA GCT CAT CAA GCG CAA GAA TAC GCT       869
Pro Ala His Val Pro Glu Glu Val Ala His Gln Ala Gln Glu Tyr Ala
            610                 615                 620

AAA AAA GCG TAT ATT ATG TTA GAT GGA AGT GGC TTA AGT CGC TGT GAT       917
Lys Lys Ala Tyr Ile Met Leu Asp Gly Ser Gly Leu Ser Arg Cys Asp
            625                 630                 635

TTC TTC TTA ACA AGC AAA AAC GAA TTA TTC CTG AAT GAA TTG AAC ACC       965
Phe Phe Leu Thr Ser Lys Asn Glu Leu Phe Leu Asn Glu Leu Asn Thr
            640                 645                 650

ATG CCT GGT TTT ACT GAC TTT AGT ATG TAT CCT TTA CTG TGG GAA AAT      1013
Met Pro Gly Phe Thr Asp Phe Ser Met Tyr Pro Leu Leu Trp Glu Asn
            655                 660                 665

ATG GGC TTG AAA TAC AGT GAT TTA ATT GAG GAA CTG ATT CAG TTA GCT      1061
Met Gly Leu Lys Tyr Ser Asp Leu Ile Glu Glu Leu Ile Gln Leu Ala
670                 675                 680                 685

TTG AAT CGT TTT AAA TAA                                              1079
Leu Asn Arg Phe Lys
            690

(2) INFORMATION FOR SEQ ID NO:17:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:17:

Leu Lys Ile Ile Leu Leu Tyr Gly Gly Arg Ser Glu Glu His Asp Val
 1               5                  10                  15

Ser Val Leu Ser Ala Tyr Ser Val Leu Asn Ala Ile Tyr Tyr Lys Tyr
                20                  25                  30

Tyr Gln Val Gln Leu Val Phe Ile Ser Lys Asp Gly Gln Trp Val Lys
            35                  40                  45
```

-continued

```
Gly Pro Leu Leu Ser Glu Arg Pro Gln Asn Lys Glu Val Leu His Leu
    50                  55                  60

Thr Trp Ala Gln Thr Pro Glu Glu Thr Gly Glu Phe Ser Gly Lys Arg
65                  70                  75                  80

Ile Ser Pro Ser Glu Ile Tyr Glu Glu Glu Ala Ile Val Phe Pro Val
                85                  90                  95

Leu His Gly Pro Asn Gly Glu Asp Gly Thr Ile Gln Gly Phe Met Glu
                100                 105                 110

Thr Ile Asn Met Pro Tyr Val Gly Ala Gly Val Leu Ala Ser Val Asn
                115                 120                 125

Ala Met Asp Lys Ile Met Thr Lys Tyr Leu Leu Gln Thr Val Gly Ile
    130                 135                 140

Pro Gln Val Pro Phe Val Pro Val Leu Arg Ser Asp Trp Lys Gly Asn
145                 150                 155                 160

Pro Lys Glu Val Phe Glu Lys Cys Glu Gly Ser Leu Ile Tyr Pro Val
                165                 170                 175

Phe Val Lys Pro Ala Asn Met Gly Ser Ser Val Gly Ile Ser Lys Val
                180                 185                 190

Glu Asn Arg Glu Glu Leu Gln Glu Ala Leu Glu Glu Ala Phe Arg Tyr
    195                 200                 205

Asp Ala Arg Ala Ile Val Glu Gln Gly Ile Glu Ala Arg Glu Ile Glu
    210                 215                 220

Val Ala Ile Leu Gly Asn Glu Asp Val Arg Thr Thr Leu Pro Gly Glu
225                 230                 235                 240

Val Val Lys Asp Val Ala Phe Tyr Asp Tyr Asp Ala Lys Tyr Ile Asn
                245                 250                 255

Asn Thr Ile Glu Met Gln Ile Pro Ala His Val Pro Glu Glu Val Ala
                260                 265                 270

His Gln Ala Gln Glu Tyr Ala Lys Lys Ala Tyr Ile Met Leu Asp Gly
    275                 280                 285

Ser Gly Leu Ser Arg Cys Asp Phe Phe Leu Thr Ser Lys Asn Glu Leu
    290                 295                 300

Phe Leu Asn Glu Leu Asn Thr Met Pro Gly Phe Thr Asp Phe Ser Met
305                 310                 315                 320

Tyr Pro Leu Leu Trp Glu Asn Met Gly Leu Lys Tyr Ser Asp Leu Ile
                325                 330                 335

Glu Glu Leu Ile Gln Leu Ala Leu Asn Arg Phe Lys
                340                 345
```

NUCLEIC ACIDS CONFERRING AND INDUCIBLE RESISTANCE TO GLYCOPEPTIDES PARTICULARLY IN GRAM-POSITIVE BACTERIA

This application is a continuation of Ser. No. 08/454,196, filed on Sep. 7, 1995, U.S. Pat. No. 5,770,361, which is a 371 of PCT/FR93/01264, filed on Dec. 17, 1993.

The invention relates to the polypeptides associated with the expression of a resistance to antibiotics of the glycopeptide family, this resistance being of a type inducible by vancomycin and not inducible by teicoplanin, particular in the Gram-positive bacteria, in particular in the family of the Gram-positive cocci. The invention also relates to a nucleotide sequence coding for these polypeptides. It also relates to the use of these polypeptides and their nucleotide sequence as agents for the in vitro detection of resistance to glycopeptides. Among the Gram-positive cocci, the invention relates more particularly to the enterococci, the streptococci and the staphylococci.

The glycopeptides, which include vancomycin and teicoplanin, are antibiotic inhibitors of the synthesis of the bacterial cell wall. These antibiotics are very much used for the treatment of severe infections due to Gram-positive cocci (enterococci, streptococci and staphylococci) in particular in cases of allergy and resistance to the penicillins.

Up to 1986 vancomycin proved to be efficacious against almost all strains of enterococci.

The activity of the glycopeptides depends on the formation of a complex between the antibiotic and the peptidoglycan precursors more than on their direct interaction with enzymes of cell wall metabolism. In particular, it has been observed that the glycopeptides bind to the terminal D-alanyl-D-alanine (D-ala-D-ala) residues of the peptidoglycan precursors.

Several phenotypes of resistance to the glycopeptides have been demonstrated; in particular, strains resistant to a high level of glycopeptides and strains resistant to low concentration levels.

By strain resistant to a high level is meant a strain of bacteria, in particular a strain of Gram-positive cocci, for which the minimal inhibitory concentrations (MIC) of vancomycin and teicoplanin are higher than 32 and 8 $\mu$g/ml, respectively. The MIC of vancomycin towards strains with low-level resistance are included between 8 and 32 $\mu$g/ml. The VanB phenotype is characterized by a resistance inducible by vancomycin but not inducible by teicoplanin. Once induced, this resistance may exist against different glycopeptides, in particular against vancomycin and/or teicoplanin, and at variable levels.

The strains of enterococci corresponding to the VanB phenotype (class B) are in particular strains of *E. faecalis* and *E. faecium*.

Al-Obeid S et al. (FEMS Microbiology Letters 70 (1990) 101–106) have thus compared the resistance proteins to glycopeptides, inducible by vancomycin, in four strains of Enterococci, and have deduced from their comparison the existence of three types of proteins, one of these types being present in the *E. faecium* strain resistant to low levels of vancomycin. According to the authors of this publication, a protein of molecular weight of about 39.5 kDa is induced in the strains with low-level resistance and this resistance is linked to induction by vancomycin. These strains were also reported to exhibit a resistance to teicoplanin, also induced by vancomycin.

According to Al-Obeid et al., this protein of 39.5 kDa is present in multiple forms but the nature of this multiplicity has not been studied. According to these authors there might exist a structural specificity depending on the species of bacteria concerned and the level of resistance which needs to be confirmed.

In this publication Al-Obeid et al. described 11 amino acids of the N-terminal sequence of the protein of 39.5 kDa and observed that this sequence exhibited about 70% homology with many membrane proteins of prokaryotic or eukaryotic origin having diverse functions. According to the authors this comparison did not allow the possible function of the protein to be established. Finally, Al-Obeid et al. noticed that other proteins are induced, although to a lesser degree.

The invention relates to peptides, polypeptides or proteins implicated in the expression of a resistance to antibiotics of the glycopeptide family and in particular to vancomycin and/or teicoplanin as well as nucleotide sequences coding for such polypeptides. The resistance in question above is of a type inducible by vancomycin but not by teicoplanin.

The expressions "implicated in the expression of a resistance" or "implicated in a resistance" signify that the protein of the invention is necessary in order for the resistance to be manifest.

The invention also relates to nucleotide probes utilizable for the detection of a resistance to the glycopeptides, in particular by means of the polymerase chain reaction (PCR), or by assays involving antibodies.

Thus, the object of the invention is a VanB protein characterized in that it comprises the following amino acid sequence I, and in that it participates in the resistance to glycopeptides, in particular to vancomycin, this resistance being of a type inducible by vancomycin and not by teicoplanin in Gram-positive bacteria (SEQ ID NO: 2).

(I)

M N K I K V A I I F G G C S E E H D V S V K S A I E

I A A N I N T E K F D P H Y I G I T K N G V W K L C

K K P C T E W E A D S L P A I F S P D R K T H G L L

V M K E R E Y E T R R I D V A F P V L H G K C G E D

G A I Q G L F E L S G I P Y V G C D I Q S S A A C M

D K S L A Y I L T K N A G I A V P E F Q M I E K G D

K P E A R T L T Y P V F V K P A R S G S S F G V T K

V N S T E E L N A A I E A A G Q Y D G K I L I E Q A

I S G C E V G C A V M G N E D D L I V G E V D Q I R

L S H G I F R I H Q E N E P E K G S E N A M I I V P

A D I P V E E R N R V Q E T A K K V Y R V L G C R G

L A R V D L F L Q E D G G I V L N E V N T L P G F T

S Y S R Y P R M A A A A G I T L P A L I D S L I T L

A I E R

By the expression "inducible resistance" is meant the capacity of a specific Gram-positive bacterium, in particular of a specific Enterococcus strain, to produce a VanB protein in the presence of a concentration of 0.05 to 1$\mu$l/ml of vancomycin.

The resistance to one or more defined glycopeptides may result in the persistence of an infection due to microbes usually sensitive to the glycopeptides, or may be detected by means of an antibiogram (particularly for high levels of resistance), the MIC, hybridization with probes (after amplification by the PCR, for example).

According to a first embodiment of the invention, the VanB protein is characterized in that it is implicated in an inducible resistance to glycopeptides, and in particular to vancomycin, in enterococci and for example in strains of the genus E. faecium or E. faecalis.

The invention also relates to a VanB protein characterized in that it comprises an amino acid sequence modified with respect to sequence I by deletion, insertion, or replacement of one or more amino acids, provided that the VanB protein thus modified is implicated in Gram-positive bacteria in a resistance to glycopeptides, in particular to vancomycin, this resistance being of a type inducible by vancomycin, but not inducible by teicoplanin.

Also included in the framework of the invention is any peptide fragment of the VanB protein characterized in that it corresponds to the amino acid sequence I or any part of this sequence functionally associated with the inducible resistance to glycopeptides, in particular to vancomycin, in Gram-positive bacteria, for example bacteria of the family of the enterococci.

Advantageously peptide fragments of the invention exhibit additionally or alternatively antigenic properties and are hence recognized by antibodies formed against the VanB protein.

A particular fragment of sequence I corresponds for example to the following sequence or includes this sequence (residues 110–305 of SEQ ID NO: 2).

L F E L S G I P Y V G C D I Q S S A A C M D K S L A

Y I L T K N A G I A V P E F Q M I E K G D K P E A R

T L T Y P V F V K P A R S G S S F G V T K V N S T E

E L N A A I E A A G Q Y D G K I L I E Q A I S G C E

V G C A V M G N E D D L I V G E V D Q I R L S H G I

F R I H Q E N E P E K G S E N A M I I V P A D I P V

E E R N R V Q E T A K K V Y R V L G C R G L A R V D

L F L Q E D G G I V L N E V

According to another embodiment of the invention, these antigens are specific for the VanB protein and thus not recognized by antibodies recognizing the VanA and VanC proteins such as described in the patent application EP 91920753.

In addition the invention relates to a nucleotide sequence characterized in that it codes for a VanB protein implicated in resistance to glycopeptides, in particular to vancomycin, in Gram-positive bacteria, this resistance being of a type inducible by vancomycin but not inducible by teicoplanin, said VanB protein comprising the amino acid sequence I, or in that it is a DNA sequence complementary to this coding sequence, or a corresponding RNA sequence.

By complementary sequence is meant any DNA sequence whose nucleotides are complementary to those of sequence I and whose orientation is reversed.

A particular nucleotide sequence corresponding to this definition is characterized in that it comprises the following nucleotide sequence II or a nucleotide sequence modified with respect to II provided that it codes for a protein implicated in resistance to glycopeptides, in particular to vancomycin, in Gram-positive bacteria, this resistance being of a type inducible by vancomycin but not inducible by teicoplanin (SEQ ID NO: 1).

(II)

GAGCGTGTGCTGCGAGATACCACAGAAAACAATCAGAATTGTCTTAACTTT

GAAAGGAGTTTACAGCATGAATAAAATAAAAGTCGCAATTATCTTCGGCGG

TTGCTCGGAGGAACATGATGTGTCGGTAAAATCCGCAATAGAAATTGCTGC

GAACATTAATACTGAAAAATTCGATCCGCACTACATCGGAATTACAAAAAA

CGGCGTATGGAAGCTATGCAAGAAGCCATGTACGGAATGGGAAGCCGATAG

TCTCCCCGCCATATTCTCCCCGGATAGGAAAACGCATGGTCTGCTTGTCAT

GAAAGAAAGAGAATACGAAACTCGGCGTATTGACGTGGCTTTCCCGGTTTT

GCATGGCAAATGCGGGGAGGATGGTGCGATACAGGGTCTGTTTGAATTGTC

TGGTATCCCCTATGTAGGCTGCGATATTCAAAGCTCCGCAGCTTGCATGGA

CAAATCACTGGCCTACATTCTTACAAAAAATGCGGGCATCGCCGTCCCCGA

ATTTCAAATGATTGAAAAAGGTGACAAACCGGAGGCGAGGACGCTTACCTA

CCCTGTCTTTGTGAAGCCGGCACGGTCAGGTTCGTCCTTTGGCGTAACCAA

AGTAAACAGTACGGAAGAACTAAACGCTGCGATAGAAGCAGCAGGACAATA

TGATGGAAAAATCTTAATTGAGCAAGCGATTTCGGGCTGTGAGGTCGGCTG

CGCGGTCATGGGAAACGAGGATGATTTGATTGTCGGCGAAGTGGATCAAAT

CCGGTTGAGCCACGGTATCTTCCGCATCCATCAGGAAAACGAGCCGGAAAA

AGGCTCAGAGAATGCGATGATTATCGTTCCAGCAGACATTCCGGTCGAGGA

ACGAAATCGGGTGCAAGAAACGGCAAAGAAAGTATATCGGGTGCTTGGATG

CAGAGGGCTTGCTCGTGTTGATCTTTTTTTGCAGGAGGATGGCGGCATCGT

TCTAAACGAGGTCCAATACCCTGCCCGGTTTTACATCGTACAGCCGCTATC

CACGCATGGCGGCTGCCGCAGGAATCACGCTTCCCGCACTAATTGACAGCC

TGATTACATTGGCGATAGAGAGGTGACCCGTATGGAAAATGGTTTTTTGT

TTTTTAGATGAAATGTTGCA

Generally speaking the object of the invention is also a nucleotide fragment characterized in that it is capable of hybridizing under stringent conditions with a sequence such as defined in sequence II above.

The stringent conditions are the following:
reaction temperature of 65° C. overnight in a solution containing 0.1% SDS, 0.7% skimmed milk powder, 6×SSC (1×SSC=0.15M NaCl and 0.015M sodium citrate at pH=7.0)
washes at room temperature in 2×SSC-0.1% SDS, then at 65° C. in 0.2 SSC-0.1% SDS.

Advantageously a nucleotide fragment corresponding to the previous definition will have at least 15 nucleotides, and preferably at least 20.

For this purpose a particular nucleotide sequence comprises the following sequence (SEQ ID NO: 3).

TCTGTTTGAATTGTCTGGTATCCCCTATGTAGGCTGCGATATT

CAAAGCTCCGCAGCTTGCATGGACAAATCACTGGCCTACATTCTTACAAAA

AATGCGGGCATCGCCGTCCCCGAATTTCAAATGATTGAAAAAGGTGACAAA

CCGGAGGCGAGGACGCTTACCTACCCTGTCTTTGTGAAGCCGGCACGGTCA

GGTTCGTCCTTTGGCGTAACCAAAGTAAACAGTACGGAAGAACTAAACGCT

-continued

```
GCGATAGAAGCAGCAGGACAATATGATGGAAAAATCTTAATTGAGCAAGCG

ATTTCGGGCTGTGAGGTCGGCTGCGCGGTCATGGGAAACGAGGATGATTTG

ATTGTCGGCGAAGTGGATCAAATCCGGTTGAGCCACGGTATCTTCCGCATC

CATCAGGAAAACGAGCCGGAAAAAGGCTCAGAGAATGCGATGATTATCGTT

CCAGCAGACATTCCGGTCGAGGAACGAAATCGGGTGCAAGAAACGGCAAAG

AAAGTATATCGGGTGCTTGGATGCAGAGGGCTTGCTCGTGTTGATCTTTTT

TTGCAGGAGGATGGCGGCATCGTTCTAAACGAGGTC
```

The peptides and polypeptides of the invention make it possible to define a genotypic class, characterized by the capacity of the nucleotide sequences coding for these peptides to hybridize under stringent conditions with the sequance II constituting a probe.

These fragments may be used as primers for carrying out amplification reactions, or as probes.

Particularly valuable probes correspond to the following sequences (SEQ ID NO: 4–5):
  primer 1:5' ATGGGAAGCCGATAGTC 3', (positions 241–258 of nucleotides of sequence I)
  primer 2:5' GATTTCGTTCCTCGACC 3' (complementary reverse sequence of the nucleotide fragment 860–877 of sequence I).

Nucleotide probes according to the invention may be specific for the detection in Gram-positive bacteria of sequences coding for a VanB protein implicated in the resistance to glycopeptides, in particular to vancomycin and/or teicoplanin, this resistance being inducible in conformity with the previous definition, these probes being in addition universal among these sequences.

By probes specific for VanB is meant any oligonucleotide hybridizing with a nucleotide sequence coding for a VanB protein according to the invention as described in the preceding pages, and not exhibiting cross-hybridization or amplification (PCR) reactions with sequences present in all of the sensitive strains.

A particular nucleotide fragment according to the invention is characterized in that it does not hybridize under stringent conditions with the DNA of strains of enterococci sensitive to vancomycin, in particular with the DNA of the strains *E. faecalis* JH2-2 and *E. faecium* BM4107.

These reference strains have been described by Jacobs and Hobbs (J. Bacteriol. 117 1974, 360–372) and Leclercq et al. (Antimicrob. Agents Chemother. 33 1989), respectively.

Another useful nucleotide fragment in the framework of the invention is specific for the vanB gene to the extent that it does not hybridize under stringent conditions with the vanA and vanC genes as described in the PCT application 91920753.

A particularly useful nucleotide fragment in the framework of the invention is the fragment corresponding to sequence II.

This fragment is an internal fragment derived from the gene implicated in the resistance to strains of enterococci. The resistance may exist at variable concentration levels of glycopeptides.

The invention also relates to nucleotide fragments modified with respect to the foregoing by mutation, addition or deletion of nucleotides, provided that the fragment thus modified either codes for a fragment of the functional VanB protein as regards its property of the resistance to glycopeptides, in particular to vancomycin, under conditions described above, or hybridizes with the vanB gene.

Should the nucleotide fragments be used as probes, labelling is performed by the standard techniques. As examples, radioactive or enzymatic markers should be used.

Nucleotide fragments according to the invention may be used as primers to carry out the amplification of the nucleic acid contained in a given biological sample, for example by PCR.

Moreover, the invention relates to a recombinant DNA sequence characterized in that it comprises a nucleotide sequence described above under the control of regulatory elements likely to be involved in the cloning and expression of a gene implicated in a resistance, of a type inducible by vancomycin and not inducible by teicoplanin, to antibiotics of the glycopeptide family, in particular vancomycin, in a defined host.

This gene implicated in the resistance is for example the vanB gene which comprises the nucleotide sequence II or any functional part in terms of inducible resistance derived from a sequence hybridizing with sequence II.

The invention also relates to a recombinant vector for the cloning and expression, characterized in that it comprises a nucleotide sequence described above at a site inessential for its replication, optionally under the control of regulatory elements likely to be involved in the expression of a resistance, of a type inducible by vancomycin and not by teicoplanin, to antibiotics of the glycopeptide family, in particular vancomycin, in a defined host.

Particular vectors are for example plasmids, phages, cosmids, YACs.

A preferred vector is the plasmid pAT201 deposited with the C.N.C.M. on Dec. 11, 1992 under the number I-1277.

Another preferred vector is the plasmid pAT202 formed from the plasmid pUC19Ω containing a 3.3 kb fragment containing the vanB gene of *Enterococus faecalis* V583 (HindIII/KpnI).

pAT202 was introduced into *E. coli* JM83 and deposited with the C.N.C.M. on Mar. 29, 1993 under the number I-1291 (identification *E. coli* BM2973).

These vectors may be used to transform or transfect cell hosts in order to clone or express the nucleotide sequences of the invention.

A recombinant cell host according to the invention is characterized in that it is modified by a nucleotide sequence or a vector described above.

The cell host is preferably modified by this sequence under conditions permitting the expression of a functional VanB protein as regards inducible resistance to glycopeptides.

The object of the invention is also a recombinant VanB protein such as obtained from a recombinant cell host according to the previous definition, the VanB protein obtained being characterized in that its peptide skeleton comprises the above amino acid sequence, and in that it is implicated in a resistance to glycopeptides, in particular to vancomycin, in Gram-positive bacteria, this resistance being of a type inducible by vancomycin but not inducible by teicoplanin.

The VanB protein according to the invention makes it possible to prepare monoclonal or polyclonal antibodies characterized in that they recognize specifically the VanB protein or a peptide fragment described above.

These antibodies may be obtained according to the standard methods for the production of antibodies. In particular for the preparation of the monoclonal antibodies recourse should be had to the method of Köhler and Milstein according to which monoclonal antibodies are prepared by cell fusion between myeloma cells and spleen cells of mice previously immunized with a polypeptide or a composition according to the invention, in conformity with the standard procedure.

The antibodies of the invention can advantageously be used for the detection of the presence of proteins characteristic of a resistance to the glycopeptides, in particular to vancomycin and teicoplanin, this resistance being of the type inducible by vancomycin but not inducible by teicoplanin.

Also included in the framework of the invention is a kit for the in vitro diagnosis in a biological sample of the presence of strains resistant to glycopeptides after induction, in particular by vancomycin but not by teicoplanin, these strains belonging in particular to the Gram-positive cocci, in particular in that they are strains of enterococci, for example E. faecium, characterized in that it contains:

optionally labelled antibodies described above, a reagent for the detection of an inmmunological reaction of the antigen-antibody type, optionally, reagents for lysing the cells of the tested sample, optionally, a defined concentration of vancomycin to induce resistance.

The invention also relates to a kit such as that defined above which contains in addition antibodies specifically directed against the VanA protein and/or antibodies specifically directed against the VanC protein.

According to another embodiment of the invention, the kit enables resistance corresponding to a phenotype VanA, VanB or VanC to be detected indiscriminately and contains antibodies recognizing VanA, VanB and VanC. These antibodies may be selected by their capacity to recognize an epitope common to the three proteins. It may also be a mixture of antibodies recognizing different epitopes, specific to each of the proteins.

According to another embodiment of the invention, a kit for the in vitro diagnosis of the presence of strains resistant to low levels of glycopeptides, resistant in particular to vancomycin, is characterized in that it contains:

a nucleotide probe capable of hybridizing under stringent conditions with a nucleotide sequence of the vanB gene, and optionally, nucleoside triphosphates dATP, dCTP, dTTP, dGTP, a DNA polymerase.

Another detection kit contains in addition nucleotides capable of hybridizing specifically with the vanA gene and a probe capable of hybridizing specifically with the vanC gene.

This kit may be advantageously used for the detection of a resistance in Gram-positive cocci, in particular in enterococci, for example in E. faecium.

The invention also relates to a kit for the in vitro detection of a resistance to glycopeptides, in particular to vancomycin, this resistance corresponding to one of the phenotypes VanA, VanB or VanC, the kit containing:

a nucleotide probe hybridizing with the genes vanA, vanB and vanC, nucleoside triphosphates dATP, dCTP, dTTP and dGTP, a DNA polymerase.

The invention also relates to a procedure for the in vitro detection of the presence of strains resistant to glycopeptides, in particular to vancomycin and/or teicoplanin, these strains belonging in particular to the family of the Gram-positive cocci, in particular in that they are strains of enterococci, for example E. faecium or E. faecalis, characterized in that it comprises:

a) the placing of a biological sample likely to contain the resistant strains in contact with a primer constituted by a nucleotide fragment according to the invention such as that described above, capable of hybridizing with the nucleotide sequence under investigation and implicated in the expression of the resistance, this sequence being used as matrix in the presence of the 4 different nucleoside phosphates and a polymerase under conditions of hybridization such that for each nucleotide sequence having hybridized with a primer, an elongation product of each primer complementary to the matrix is synthesized, b) the separation of the matrix from the elongation product obtained, this latter being then also able to behave as a matrix, c) repetition of step a) so as to obtain a detectable quantity of the nucleotide sequences investigated, d) the detection of the amplification product of the nucleotide sequences.

The probe used may thus be specific for the nucleotide sequence II or a sequence hybridizing with sequence II under stringent conditions. Under these conditions the procedure according to the invention makes possible the detection of a resistance to glycopeptides, this resistance being inducible by vancomycin but not inducible by teicoplanin.

According to a particular embodiment of the invention, this procedure also comprises the placing of the biological sample in contact with a specific nucleotide fragment of the vanA gene and/or a specific nucleotide fragment of the vanC gene. In this case the procedure according to the invention advantageously makes possible the detection of different phenotypes of resistance.

According to another embodiment, a resistance corresponding to a phenotype VanA, VanB or VanC will de detected indiscriminately by using a probe common to the genes vanA, vanB or vanC. Such a probe may be constructed from the aligned polypeptide sequences of FIG. 2.

Other characteristics and advantages of the invention will become apparent in the following Examples and Figures:

FIGURES

FIG. 1

Nucleotide and amino acid sequences corresponding to the vanB gene (SEQ ID NO: 1–2). The nucleotide sequences of the two strands was determined from the insert contained in pUC18 by the dideoxy chain termination method (Sanger et al., 1977, Proc. Natl. Acad. Sci. USA, 74:5463–5467) using T7 DNA polymerase. The RBS sequence underlined represents the Shine-Dalgarno sequence for ribosome binding.

FIG. 2

Alignment of the deduced amino acid sequence of the VanB protein and corresponding regions of VanA, VanC, DdlA and DdlB of E. coli (Dutka-Malen et al., 1992 Gene, 112:53–58), Ddl of E. faecalis V583 and DdlA of S. typhimurium (Daub et al., Biochemistry 27, 1988, 3701–3708) (SEQ ID NO: 2, 6–11). The identical amino acids (I) and the conservative substitutions (C) in the 7 sequences have been indicated beneath the alignment. In order to permit the classification of conservative substitutions, the amino acids have been regrouped as follows: RK, LFPMVI, STQNC, AGW, H, ED and Y. The domains 1, 2, 3 and 4 correspond to regions of high homology.

FIG. 3

Oligonucleotides V1 and V2 used to amplify the DNA of the vanB gene (SEQ ID NO: 12–15).

FIG. 4

Nucleotide sequence of the ddl gene of *E. faecalis* V583 and the corresponding amino acid sequence (SEQ ID NO: 16–19). The plasmid pAT203 was constructed by subcloning the DNA of λ recombinant bacteriophage partially digested with Sau3AI (Pharmacia) in pUC19 digested with BamHI (Pharmacia). The 15 kb insert of pAT203 contains the ddl gene. The nucleotide sequence of 1079 consecutive bp of pAT203 was determined on both strands by the dideoxy chain termination method. The first base pair of the sequence is defined as position 1. The ribsosme binding sequence RBS is at position 19 upstream from the start codon TTG. The stop codon TTA is indicated. The deduced amino acid sequence of the Ddl protein is shown.

EXPERIMENTAL APPROACH

The antibiotics of the glycopeptide family such as vancomycin (Vm) and teicoplanin (Te) bind to the C-terminal D-Ala residues of the peptidoglycan precursors, thus blocking their incorporation into the bacterial cell wall (Reynolds, P. E. 1989 Eur. J. Clin. Microb. Infect. Dis. 8:943–950). The D-Ala residues are incorporated into the precursors of the cell wall in the form of dipeptides synthesized by D-Ala:D-ala ligases (DDL) (Walsh, C. T. 1989 J. Biol. Chem. 264:2393–2396). The VanA ligase synthesizes the dipeptide D-Ala-D-lac which substitutes for D-Ala-D-Ala leading to the synthesis of precursors which bind vancomycin with reduced affinity (Bugg et al., Biochemistry 30:10408–10415 (1991), Handwerger et al., J. Bacteriol. 174:5982–5984 (1992), Messer et Reynolds, FEMS Microbiol. Letters 94:195–200 (1992)).

The resistance to the glycopeptides in the enterococci is heterogeneous (Dutka-Male et al., 1990 Antimicrobiol Agents Chemother. 34:1875–1879).

The resistance proteins VanA and VanC (see patent application EP 91920753.0 of Oct. 29, 1991) show a 30 to 37% homology (the details are given in Table III) with the amino acids of the D-Ala: D-Ala ligases (Ala=alanine) of *E. coli* (Dutka-Malen et al., 1992 Gene 112:53–58). The structural genes for the VanA and VanC proteins do not hybridize with the DNA of the strains with the VanB phenotype (Dutka-Malen et al., 1990, Leclercq et al., Antimicrob. Agents Chemother. 36:2005–2008 (1992)).

The inventors have succeeded in identifying the nucleotide sequence implicated in the properties of resistance to vancomycin of strains of enterococci having the VanB phenotype and resistant after induction with vancomycin.

Bacterial strains: 39 isolates of *E. faecium* (28 strains) and *E. faecalis* (11 strains) resistant to low and high concentrations of vancomycin and sensitive to teicoplanin were studied (Table II). Among these strains 24 isolates including *E. faecalis* V583 (Sahm D. et al., Antimicrob. Agents Chemother. 1989, 33:1588–91) and *E. faecium* D366 (Gutmann L. et al., Antimicrob. Agents Chemother. 1992, 36:77–80) were resistant to low concentrations of vancomycin on the basis of a disk sensitivity test. These strains belong to the class B phenotype. 15 isolates resistant to high concentrations of vancomycin (MIC≧128 μg/ml) including *E. faecalis* strain V583-2 (Zarlenga L. J. et al., Antimicrob. Agents Chemother. 1992, 36:902–5), which is a spontaneous mutant of V553 as well as UMH-1 (Schwalbe R. et al., Abstract A-117, in Abstracts of the 91st General Meeting of the American Society for Microbiology, Dallas, Tex.: American Society for Microbiology, 1991) were also studied. The control strains were well-characterized strains of enterococci belonging to the phenotypes A and C and hybridizing with the probes VanA and VanC, respectively. In particular there are 6 clinical isolates of *E. faecium* highly resistant to vancomycin and to teicoplanin, including BM4147. The strains of *E. gallinarum* including BM4147 belonging to class C were also used as controls. Strains of *E. casseliflavus* are also used as controls, including the strain ATCC 25788, which are isolates intrinsically resistant to low levels of vancomycin and sensitive to teicoplanin (Leclercq R. et al., Antimicrob. Agents Chemother. 1992, 36:2005–8).

The following strains were also studied: *Erysipelothrix rhusiopathiae* A124 (Institute Pasteur collection), *Lactobacillus brevis* ATCC 14869, *Lactobacillus casei* ATCC 393, *Lactobacillus confusus* ATCC 10881, *Lactobacillus fermentum* ATCC 9338, *Lactobacillus plantarum* ATCC 8014, *Lactobacillus reuteri* ATCC 23272, *Lactobacillus rhamnosus* ATCC 7469, *Lactobacillus salivarius* ATCC 11741, *Pediococcus acidilacti* ATCC 8042, *Pediococcus pentosaceus* ATCC 33316, and *Leuconostoc mesenteroides* CIP 16407. The following enterococci sensitive to antibiotics of the glycopeptide family are used as negative controls: *E. durans* ATCC 19432, *E. faecium* ATCC 19434, BM4107 (Leclercq R et al., Antimicrob Agents Chemother. 1992, 36:2005–8), and MT10R (Gutmann L et al., Antimicrob. Agents Chemother., 1992, 36:77–80), strain sensitive to vancomycin derived from D366; *E. faecalis* ATCC 29212, ATCC 33186, JH2-2 (Leclercq R et al., Antimicrob. Agents Chemother. 1992, 36:2005–8) and V583-C1, strain sensitive to vancomycin derived from V583 (Table II) and a clinical isolate of *E. faecium* and *E. faecalis*. Characteristics of reference strains are depicted in Table I. *E. faecium* BM4107 and *E. faecalis* JH2-2, resistant to both rifampin and fusidic acid (Leclercq R et al., Antimicrob. Agents Chemother. 1992, 36:2005–8) were used as receptor strains for conjugation experiments.

Identification of the Enterococci

The enterococci were identified by the method of Facklam and Collins, J. Clin. Microbiol. 1989, 27:731–4). The identification of the species was based on the tests of potassium tellurite reduction and the production of acids from carbohydrates on bands of API 20 streptococci (bioMérieux, Marcy l' Etoile, France). The tests of mobility at 30° C. and fermentation of carbohydrates were used to distinguish *E. gallinarum* and *E. casseliflavus* from *E. faecium* and *E. faecalis*. The strains of *E. casseliflavus* were distinguished from the strains of *E. gallinarum* on the basis of the production of a yellow pigment on the agar.

Medium

A brain-heart medium and agar (Difco Laboratories, Detroit, Mich.) were used. Sensitivity tests were performed on Mueller-Hinton agar (Diagnostics Pasteur, Marne LaCoquette, France). All of the incubations were performed at 37° C.

Determination of the In Vitro Sensitivity to the Antibiotics.

The disk diffusion test with disks containing 30 μg of vancomycin or 30 μg of teicoplanin (Diagnostics Pasteur) was used for the initial screening. The method of Steers et al. with $10^4$ CFU per spot was used to determine the MIC of the antibiotics (Steers E. et al., Antibiot. Chemother. (Basel) 1959, 9:307–11)

Transfer of the Character of Resistance to an Antibiotic

The conjugation on filters was carried out according to the procedure described by Dutka-Malen S. et al., Antimicrob. Agents Chemother. 1990, 34:1875–9. The antibiotic concentrations for the selection of the transconjugates were the following: rifampin: 20 μg/ml; fusidic acid: 10 μg/ml and vancomycin: 4 and 8 μg/ml.

Enzymes and Reagents

Lysozyme was obtained from the Sigma Chemical Co.(St. Louis, Mo.). RNase A (bovine pancreas) and proteinase K were obtained from Calbiochem. Co.(San Diego, Calif.). {$\alpha$-$^{32}$P} dCTP and the triethylammonium salt (specific activity 3000 CI/mmol) were obtained from the Radiochemical Center, Amersham, Great Britain. Teicoplanin was obtained from Gruppo Lepetit (Milan, Italy) and vancomycin was obtained from Eli Lilly & Co (Indianapolis, Ind.).

The oligonucleotides V1 and V2 described in the patent application EP 91920753.0 made possible the amplification by means of the PCR technique of fragments internal to the genes coding for the proteins VanA, VanC and D-Ala: D-Ala ligases (Dutka-Malen et al., 1992 Gene 112:53–58).

The amplification of the vanB gene was carried out with the oligonucleotides V1 and V2 and the DNA (20 ng) of *Enterococcus faecalis* V583 (Sahm et al., 1989 Antimicrob. Agents Chemother.33:1588–1591).

To carry out this amplification the technique described in the publication of Dutka-Malen et al., 1992 was used. The fragments obtained were separated on agarose gel (1%) in a TAE buffer which made it possible to reveal a unique band of about 600 bp which was extracted from the gel using a DNA purification kit (GeneClean, Bio101 Inc., La Jolla, Calif.). By using a kit leading to the production of blunt ends on the DNA (Amersham, Amersham, Great Britain), the fragments were treated with the T4 DNA polymerase and ligated at the SmaI site of a digested and dephosphorylated pUC18 plasmid (Norrander et al., 1983, Gene 26:101–106).

The sequence of 632 bp (vanB probe) corresponding to the insert of the recombinant plasmid (FIG. 1) was determined by the dideoxy chain termination method (Sanger et al., 1977, Proc. Natl. ACad. Sci. USA, 74:5463–5467) using T7 DNA polymerase (Pharmacia, Uppsala, Sweden) and {$\alpha$-$^{35}$S} dATP (Amersham Radiochemical Center, Amersham Great Britain).

Given that the amplification with the Taq DNA polymerase may lead to erroneous incorporations of nucleotides, the sequence was confirmed as follows: an oligonucleotide complementary to the positions 513 to 530 of the nucleotide sequence shown in FIG. 1 was synthesized by the phosphoramidite method (Organic Chemistry unit, Pasteur Institute, France) and used with the primer V1 to carry out an amplification of a vanB fragment by PCR. The PCR product was sequenced directly (Mabilat et al., 1990, Plasmid 23:27–34) or after the cloning in a pUC18 vector in order to reveal the identity of the nucleotides with the cloned fragment obtained with V1 and V2.

A Southern hybridization was carried out according to the method of Johnson et al., Gene Anal. Technol. 1:3–8 (1984). The total DNA of the strains of enterococci (Table 1) was prepared according to the procedure described by Le Bouguenec et al., 1990, J. Bacteriol. 172:727–734, digested with the enzymes HindIII and KpnI (United States Biochemical corporation, Cleveland, Ohio) and resolved on 1% agarose gels. The DNA was transferred to nylon membranes (Nytran, Schleicher & Schuell, Dassel, Germany) with a transfer apparatus under vacuum (Trans. Vac. TE80, Hoefer Scientific Instruments, San Francisco, Calif.). The probe was obtained by labelling the cloned PCR fragment with a nick translation kit (Bethesda Research Laboratories Life Technologies Inc., Gaithersburg, Md.) and {$\alpha$-$^{32}$P} dCTP (Amersham Radiochemical Center, Amersham, Great Britain). The hybridization was carried out under stringent conditions at 68° C. (Johnson et al., 1984, Gene Anal. Technol. 1:3–8). The membranes were washed at 65° C. in 0.1% SDS-2×SSC.

The vanA probe consisted of a PstI fragment of 265 bp internal to the vanA gene (Dukta-Malen S et al., Mol. Gen. Genet. 1990, 224:364–372). The vanC probe consisted of a EcoRI-HincII fragment of 690 bp internal to the vanC gene (Leclercq R et al., Antimicrob. Agents Chemother. 1992, 36:2005–8. Dukta-Malen S. et al. Gene, 1992, 112:53–58). The vanB probe corresponds to the sequence II.

The amino acid sequence deduced for the insert contained in the pUC18 plasmid was compared with different protein sequences (FIG. 2): Table 5 summarises the identity percentages of amino acids when the protein sequences VanB, VanA, VanC, ElDdl, DdlA and DdlB are compared pairwise.

Under the conditions of Southern hybridization the cloned fragment hybridized with the 3.3 kb HindIII-KpnI fragment of *E. faecalis* V583. The probe does not hybridize with the DNA of a vancomycin-sensitive derivative of V583 or with the DNA of the *E. faecalis* and *E. faecium* strains sensitive to vancomycin used as reference. The cloned DNA fragment obtained by PCR corresponds to an internal fragment of the gene implicated in the resistance. This gene codes for the enzyme related to the D-Ala: D-Ala ligases, called VanB, which might be implicated in the synthesis of a product substituting for D-Ala-D-Ala.

These tests have made it possible to demonstrate a single group of genes related to vanB and responsible for a low- and high-level resistance to vancomycin in the enterococci (Tables 1 and 2).

No hybridization was observed between the VanB probe and the DNA of strains sensitive to vancomycin without induction or bearing the vanA or vanC genes or intrinsically resistant.

The complete sequence of the vanB gene was cloned by implementing the following steps:

The plasmid pAT202 was obtained by subcloning in pUC19 a 3.3 kb HindIII-KpnI fragment of the λ recombinant bacteriophage containing the vanB gene The cloning was performed with restriction endonucleases (Boehringer, Mannheim, Germany and Pharmacia LKB Biotechnology Inc. Uppsala, Sweden), T4 DNA ligase (Boehringer) and alkaline phosphatase (Pharmacia) in conformity with the recommendations of the manufacturer. The nucleotide sequence of the consecutive 1090 bp of pAT202 was determined on both strands by the dideoxy chain termination method (Sanger et al., 1977) using a modified T7 DNA polymerase (Amersham Radiochemical Center, Amersham, Great Britain) and complementary oligonucleotides of the sequence, synthesized by the methoxy phosphoramidite method (Institute Pasteur, Paris, France). The reaction products were resolved by electrophoresis on a 6% denaturing polyacrylamide gel. The first base pair of the sequence shown corresponds to position 1 (FIG. 1). The potential ribosome binding site (RBS) (Moran et al., Mol. Gen. Genet. 186 (1982) 339–346) upstream from the ATG initiation codon at position 46 is underlined. The stop codon (TGA) is indicated by an asterisk. The amino acid sequence is aligned with the first nucleotide of each codon.

The transfer of the vancomycin-resistance character (in 6 isolates of enterococci out of 17) by conjugation on a filter was observed in *E. faecium* and *E. faecalis* strains resistant to low or high concentrations of antibiotics.

Of the other fragments of about 600 bp amplified from the oligonucleotides V1 and V2, an insert hybridized with the DNA of Vm$^R$ or Vm$^S$ strains of *E. faecalis* but not with the DNA of strains of 18 other species. This gene codes for a D-Ala: D-ala ligase in *E. faecalis*. Since no other ligase gene was detected in *E. faecalis*, this gene was called ddl.

The cloning and sequencing of the ddl gene inserted in the pUC19 vector (Norrander et al., Gene 26, 1983, 101–106)

led to the observation that the content of the bases G and C in ddl (37.5%) and the chromosome of E. faecalis (37–39%) were very similar.

Different observations suggest that the vanB gene might have an exogenous origin: (i) The gene may be transferred by conjugation. (ii) The nucleotide sequences related to vanB have not been detected in the DNA of Vm$^S$ strains of E. faecalis and E. faecium and the representatives of 16 other species of Enterococcus (Table III). (iii) The GC base content of the vanB gene differs markedly from that of the chromosome of E. faecalis. (iv) The low level of similarity between Ddl of E. faecalis and VanB (34% identity) indicates that the corresponding genes have not originated as the result of a recent duplication.

Precursors of Peptidoglycans in E. faecalis Vm$^R$ and Vm$^S$

The incubation of E. faecalis V583 before the induction of the Vm$^R$ or Vm$^S$ strains of E. faecalis JH2-2 (Jacob and Hobbs, J. Bacteriol. 117, 1974, 360–372) with the cell wall inhibitor ramoplanin (9 ug/ml) led to the accumulation of the cell wall precursor UDP-N-acetyl-muramyl-L-Ala-D-Glu-L-Lys-D-Ala-D-Ala (UDP-Mur-NAc-pentapeptide) which is used in the normal cycle of peptidoglycan synthesis.

After the induction of resistance, E. faecalis V583 accumulated three cell wall intermediates when the strain was incubated with ramoplanin (Table IV). These intermediates were identified as being UDP-MurNAc-pentapeptides, UDP-MurNAc-tetrapeptides lacking the C-terminal D-Ala residue of the UDP-MurNAc-pentapeptide; and predominantly UDP-MurNAc-tetrapeptide-D-lactate in which the C-terminal D-Ala residue of the UDP-MurNAc-pentapeptide is replaced by D-lactate. The presence of UDP-MurNAc-tetrapeptide-D-lactate suggests that the strains of the VanA and VanB phenotypes have the same basic resistance mechanism to the glycopeptides; i.e. they synthesize D-lactate which may be linked to VanB (or VanA) by D-Ala to synthesize D-Ala-D-lactate which is then incorporated into the peptidoglycan precursor.

The wall precursors were purified by ion exchange chromatography and desalting by gel filtration. The identification was based on mass spectrometry (positive ion electrospray mass spectroscopy), a UV spectrum (for the uracil) automated amino acid analysis after hydrolysis for 4 h and 24 h (for muramic acid and the ratios of the amino acids) and the analysis by specific enzymatic reactions of the terminal residue carried out by reaction with D, D-carboxypeptidase of Actinomadura R39 (Messer and Reynolds, FEMS Microbiol. Letter 94 1992, 195–200).

The total quantity of precursors accumulated in each culture was approximately the same 65 μmol/g of dry weight during an incubation period corresponding to 0.6 of the mean synthesis time.

TABLE I

Bacterial strains

| | MIC (μg/ml) | | Hybridization with the vanB probe | | | |
|---|---|---|---|---|---|---|
| Strain | Vm | Te | vanA | vanB | vanC | Reference |
| E. faecalis | | | | | | |
| V583 | 64 | 0,5 | – | + | – | Sahm et al (1989) |
| V583-C1 | 2 | 0,5 | – | – | – | D. F. Sahm |
| V583-2 | 1024 | 1,0 | – | + | – | Zarlenga LJ (1992) |
| UMH-1 | 1024 | 1,0 | – | + | – | Schwalbe et al (1991) |
| ATCC 29212 | 2 | 0,5 | – | – | – | |

TABLE I-continued

Bacterial strains

| | MIC (μg/ml) | | Hybridization with the vanB probe | | | |
|---|---|---|---|---|---|---|
| Strain | Vm | Te | vanA | vanB | vanC | Reference |
| E. faecium | | | | | | |
| D366 | 32 | 0,5 | – | + | – | Gutmann et al (1992) |
| MT10R | 2 | 0,25 | – | – | – | Gutmann et al (1992) |
| BM4147 | 1024 | 512 | + | – | – | Dutka-Malen et al (1990) |
| ATCC 19434 | 1 | 1 | – | – | – | |
| E. gallinarum BM4174 | 8 | 1 | – | – | + | Dutka-Malen et al (1992) |
| E. casseliflavus | 8 | 1 | – | – | – | |

TABLE II

Phenotypic and genotypic classes among the Gram-positive cocci resistant to vancomycin

| PHENO-TYPIC CLASS | GENO-TYPIC CLASS (A) | SPECIES | MIC (μg/ml) | |
|---|---|---|---|---|
| | | | Vancomycin | Teicoplanin |
| Susceptible | Susceptible | Enterococcus spp. (10) | 0.5–2 | 0.25 |
| A | A | E. faecium (6) | 256–>1.000 | 64–>1.000 |
| B | B | E. faecium (28) | 4–256 | 0.5–1 |
| B | B | E. faecalis (11) | 4–1024 | 0.5–1 |
| C | C | E. gallinarum (3) | 8 | 1 |
| C | NC | E. casseliflavus (2) | 4–8 | 0.5–1 |
| NC | NC | Lactobacillus spp. (8) | >1.000 | >1.000 |
| NC | NC | Leuconostoc. sp. (1) | >1.000 | >1.000 |
| NC | NC | Pediococcus spp. (2) | >1.000 | >1.000 |
| NC | NC | E.rhusiopathiae (1) | >1.000 | >1.000 |

[a]A : hybridization with the vanA probe;
B : hybridization with the vanB probe
C : hybridization with the vanC probe;
NC : not classed

TABLE III

Results of hybridization experiments

| Species | Resistance phenotype | Number of strains tested | Hybridization with probe | |
|---|---|---|---|---|
| | | | vanB | ddl (En. faecalis) |
| En. faecalis | Vm$^R$, Te$^S$ | 11 | + | + |
| | Vm$^S$, Te$^S$ | 5 | – | + |
| En. faecium | Vm$^R$, Te$^R$ | 6 | – | – |
| | Vm$^R$, Te$^S$ | 28 | + | – |
| | Vm$^S$, Te$^S$ | 4 | – | – |
| En. gallinarum | Vm$^R$, Te$^S$ | 3 | – | – |
| En. casseliflavus | Vm$^R$, Te$^S$ | 2 | – | – |
| En. spp. (15 species[a]) | Vm$^S$, Te$^S$ | 15 | – | – |

[a]Types of strains En. avium, En. cecorum, En. columbae, En. dispar, En. durans, En. flavescens, En. hirae, En. malodorarus, En. mundrii, En. pseudoavium, En. raffinosus, En. saccharolyricus, En. seriolicida, En. solitarius et En. sulfureus.

TABLE IV

Peptidoglycan precursors in Vm^S or Vm^R strains of *En faecalis*

| Peptidoglycan precursor | Quantity of precursor (%) in *En faecalis* | | |
|---|---|---|---|
| | JH2-2 | V583 not induced | V583 induced |
| UDP-MurNAc-L-Ala-D-Glu-L-Lys-D-Ala-D-Ala | 100 | 100 | 14 |
| UDP-MurNAc-L-Ala-D-Glu-L-Lys-D-Ala | 0 | 0 | 7 |
| UDP-MurNAc-L-Ala-D-Glu-L-Lys-D-Ala-D-lactate | 0 | 0 | 79 |

TABLE V

Sequence identity between the amino acid sequences of VanB, Ddl of *En. faecalis* V583 and D-Ala:D-Ala ligases[a]

| Compared sequence[b] | Percentage identity with respect to: | | | | | |
|---|---|---|---|---|---|---|
| | VanB | VanC | EfDdl | EcDdlA | StDdlA | EcDdlB |
| VanA | 76 | 38 | 32 | 38 | 37 | 30 |
| VanB | | 38 | 34 | 38 | 38 | 32 |
| VanC | | | 34 | 34 | 34 | 36 |
| EfDdl | | | | 40 | 40 | 34 |
| EcDdlA | | | | | 90 | 35 |
| StDdlA | | | | | | 36 |

[a] Identity of pairs of sequences derived from the alignment of FIG. 2
[b] Ec, *E. coli*; Ef, *En. faecalis*; St, *S. typhimurium*

---

We claim:

1. A kit for the in vitro detection of Gram-positive cocci resistant to a glycopeptide, wherein the kit comprises a probe capable of hybridizing under stringent conditions to:
   (a) a nucleotide sequence encoding a protein comprising the amino acid sequence of SEQ ID NO:2, or
   (b) the complement of a nucleotide sequence encoding a protein comprising the amino acid sequence of SEQ ID NO:2.

2. The kit of claim 1, wherein the probe is DNA or RNA.

3. The kit of claim 1, wherein the probe comprises the nucleotide sequence of SEQ ID NO:1, SEQ ID NO:3, SEQ ID NO:4, or SEQ ID NO:5.

4. The kit of claim 1 further comprising a DNA polymerase and the nucleoside triphosphates dATP, dCTP, dTTP, and dGTP.

5. The kit of claim 1, wherein the cocci are enterococci.

6. The kit of claim 1, wherein the cocci are E. faecium.

7. The kit of claim 1, wherein the glycopeptide is vancomycin.

8. The kit of claim 1 further comprising a probe specific for the vanA gene or the vanC gene.

9. A kit for the in vitro detection of Gram-positive cocci resistant to a glycopeptide, wherein the kit comprises a probe capable of hybridizing under stringent conditions to:
   (a) a nucleotide sequence comprising the sequence of SEQ ID NO:1, or
   (b) the complement of a nucleotide sequence comprising the sequence of SEQ ID NO:1.

10. The kit of claim 9, wherein the probe is DNA or RNA.

11. The kit of claim 9, wherein the probe comprises the nucleotide sequence of SEQ ID NO:1, SEQ ID NO:3, SEQ ID NO:4, or SEQ ID NO:5.

12. The kit of claim 9 further comprising a DNA polymerase and the nucleoside triphosphates dATP, dCTP, dTTP, and dGTP.

13. The kit of claim 9, wherein the cocci are enterococci.

14. The kit of claim 9, wherein the cocci are *E. faecium*.

15. The kit of claim 9, wherein the glycopeptide is vancomycin.

16. The kit of claim 9 further comprising a probe specific for the vanA gene or the vanC gene.

17. A method for the in vitro detection of Gram-positive cocci resistant to a glycopeptide, wherein the method comprises:

(a) mixing a sample and a probe to form a mixture,
wherein the probe is capable of hybridizing under stringent conditions to (i) a nucleotide sequence encoding a protein comprising the amino acid sequence of SEQ ID NO:2, or (ii) the complement of a nucleotide sequence encoding a protein comprising the amino acid sequence of SEQ ID NO:2;

(b) subjecting the mixture to conditions sufficient to allow an elongation product of the probe to form; and (c) determining whether or not the elongation product of the probe was formed, thereby detecting a Gram-positive cocci resistant to a glycopeptide if the probe was formed.

18. The kit of claim 17, wherein the probe comprises the nucleotide sequence of SEQ ID NO:1, SEQ ID NO:3, SEQ ID NO:4, or SEQ ID NO:5.

19. The method of claim 17, wherein the glycopeptide is vancomycin or teicoplanin.

20. The method of claim 17, wherein the cocci are *E. faecium* or *E. faecalis*.

21. A method for the in vitro detection of Gram-positive cocci resistant to a glycopeptide, wherein the method comprises:

(a) mixing a sample and a probe to form a mixture,
wherein the probe is capable of hybridizing under stringent conditions to (i) a nucleotide sequence comprising the sequence of SEQ ID NO:1, or (ii) the complement of a nucleotide sequence comprising the sequence of SEQ ID NO:1;

(b) subjecting the mixture to conditions sufficient to allow an elongation product of the probe to form; and (c) determining whether or not the elongation product of the probe was formed, thereby detecting a Gram-positive cocci resistant to a glycopeptide if the probe was formed.

22. The kit of claim 21, wherein the probe comprises the nucleotide sequence of SEQ ID NO:1, SEQ ID NO:3, SEQ ID NO:4, or SEQ ID NO:5.

23. The method of claim 21, wherein the glycopeptide is vancomycin or teicoplanin.

24. The method of claim 21, wherein the cocci are *E. faecium* or *E. faecalis*.

* * * * *

UNITED STATES PATENT AND TRADEMARK OFFICE
CERTIFICATE OF CORRECTION

PATENT NO. : 6,087,106

DATED : July 11, 2000

INVENTOR(S): Michel ARTHUR, et al.

It is certified that an error appears in the above-identified patent and that said Letters Patent is hereby corrected as shown below:

On the title page, item [54], and at the top of Column 1, the title is incorrectly listed. It should read as follows:

--[54] PROTEIN CONFERRING AN INDUCIBLE RESISTANCE TO GLYCOPEPTIDES PARTICULARLY IN GRAM-POSITIVE BACTERIA

Signed and Sealed this

Tenth Day of April, 2001

*Attest:*

NICHOLAS P. GODICI

*Attesting Officer*    *Acting Director of the United States Patent and Trademark Office*